(12) United States Patent
Cannon

(10) Patent No.: US 10,914,685 B2
(45) Date of Patent: Feb. 9, 2021

(54) SYSTEMS AND METHODS OF USING UV ABSORBENT COATINGS FOR DETECTING DEFECTS IN SUBSTRATES USED TO MAKE STERILE MEDICAL DEVICE PACKAGES

(71) Applicant: Ethicon, Inc., Somerville, NJ (US)

(72) Inventor: Ian Cannon, West Chester, PA (US)

(73) Assignee: Ethicon, Inc., Somerville, NJ (US)

( * ) Notice: Subject to any disclaimer, the term of this patent is extended or adjusted under 35 U.S.C. 154(b) by 77 days.

(21) Appl. No.: 16/157,993

(22) Filed: Oct. 11, 2018

(65) Prior Publication Data

US 2020/0116647 A1   Apr. 16, 2020

(51) Int. Cl.
*G01N 21/88* (2006.01)
*G01N 21/33* (2006.01)
(Continued)

(52) U.S. Cl.
CPC ......... *G01N 21/8806* (2013.01); *G01N 21/33* (2013.01); *G01N 21/8422* (2013.01);
(Continued)

(58) Field of Classification Search
CPC .. G01N 21/8806; G01N 21/894; G01N 21/95; G01N 21/8851; G01N 21/8422;
(Continued)

(56) References Cited

U.S. PATENT DOCUMENTS 3,700,909 A   10/1972   Murray et al.
3,755,674 A    8/1973   Murray et al.
(Continued)

FOREIGN PATENT DOCUMENTS

JP   H04282441   10/1992
JP   H07311160   11/1995
(Continued)

OTHER PUBLICATIONS

Bill Letterle, Consider UV Inspection, Quality Magazine, https://www.qualitymag.com/articles/90829-consider-uv-inspection, Nov. 2, 2012, 5 pages.
(Continued)

*Primary Examiner* — Michael C Bryant

(57) ABSTRACT

A method of evaluating the integrity of a substrate used in medical device packaging include providing a flexible, porous substrate having a first major surface, and a second major surface, applying a UV absorbent layer over at least one of the first and second major surfaces of the substrate, and placing the substrate over a UV reflective surface. The method includes directing UV light toward the substrate and the UV reflective surface, whereby the UV absorbent layer absorbs light in a spectrum that matches the wavelength of the UV light, and detecting with a UV sensitive camera any UV light that is reflected from the first and second surfaces of the substrate. The substrate is rejected if the reflected UV light that is detected by the UV sensitive camera indicates that the substrate has at least one opening having a size that is greater than or equal to 10 microns. The substrate is accepted if the reflected UV light detected by the camera indicates that the substrate has no openings that are greater than or equal to 10 microns.

20 Claims, 35 Drawing Sheets

(51) Int. Cl.
*G01N 21/84* (2006.01)
*G01N 21/95* (2006.01)

(52) U.S. Cl.
CPC ......... *G01N 21/8851* (2013.01); *G01N 21/95* (2013.01); *A61M 2209/06* (2013.01); *G01N 2021/8427* (2013.01); *G01N 2021/8887* (2013.01)

(58) Field of Classification Search
CPC ........... G01N 21/33; G01N 2021/8887; G01N 2021/8427
See application file for complete search history.

(56) References Cited

U.S. PATENT DOCUMENTS

| | | | |
|---|---|---|---|
| 5,489,022 A | 2/1996 | Baker | |
| 5,940,173 A * | 8/1999 | Tomii | G01N 21/95 356/445 |
| 6,097,427 A | 8/2000 | Dey et al. | |
| 7,940,382 B2 | 5/2011 | Ikeda et al. | |
| 2004/0157333 A1 | 8/2004 | McAmish et al. | |
| 2010/0259748 A1* | 10/2010 | Suzuki | G01N 21/894 356/51 |

FOREIGN PATENT DOCUMENTS

| | | |
|---|---|---|
| JP | 2002310924 | 10/2002 |
| JP | 2004257776 | 9/2004 |
| WO | 2016102938 | 6/2016 |

OTHER PUBLICATIONS

International Search Report issued in the corresponding International Application No. PCT/IB2019/058550, dated Dec. 10, 2019, 2 pages.

\* cited by examiner

SYSTEMS AND METHODS OF USING UV ABSORBENT COATINGS FOR DETECTING DEFECTS IN SUBSTRATES USED TO MAKE STERILE MEDICAL DEVICE PACKAGES

BACKGROUND OF THE INVENTION

Field of the Invention

The present patent application is generally related to packages for medical devices, and is more specifically related to systems and methods of detecting defects in sterile medical device packages.

Description of the Related Art

The manufacture of sealed, sterile packages for medical devices requires rigorous inspection and quality control measures throughout the packaging process. In particular, manufacturing processes seek to eliminate and/or avoid the presence of defects (e.g., pinholes, tears) in the components used to make sterile, medical device packages. In many instances, inspections involve humans conducting visual inspections of the components. The use of human inspectors to perform these tasks, however, is costly and unreliable because such operators are susceptible to boredom, fatigue, and error.

There have been many efforts directed to providing systems and methods for detecting defects in medical device packages. For example, U.S. Pat. No. 3,700,909 discloses a system for detecting pinhole defects in foil material. The system includes a narrow width ultraviolet light source, corresponding ultraviolet and photomultiplier units, and associated circuitry for shaping and counting electrical pulses, which correspond to the diameter of the pinhole defects in the foil material. The system detects both the number and the size of the pinholes in the foil material.

U.S. Pat. No. 3,755,674 discloses a method of detecting pinhole defects in sheet material. In one embodiment, the sheet material is advanced through a detection plane and a modulated ultraviolet light source is directed onto the plane. The ultraviolet light is collimated in a series of vertical channels so that the light strikes the sheet material perpendicularly to the width of the material. The edges of the advancing sheet material are shielded from both ultraviolet and ambient light. The non-ultraviolet light is filtered out from beneath the material and the ultraviolet light that is transmitted through the defects in the sheet material is photomultiplied and transformed into electrical pulses. The electrical pulses are measured and accumulated as a function of pinhole defects in the advancing sheet material.

Commonly assigned U.S. Pat. No. 6,097,427 discloses a method and assemblies for detecting defects in a process for making sealed sterile packages. In one embodiment, adjacent sheets of polymer coated aluminum foils are conveyed through a sequence of steps in an apparatus which produces frames containing plastic packets of needle-suture assemblies. A vision system having video cameras connected to a specially adapted computer enables monitoring of the product traveling through the framing operation to detect various defects in the foil and in the product formation. Upon detection of a defect, the computer system can either identify and separate rejected product from good product or shut down the apparatus.

U.S. Patent Application Publication No. US 2004/0157333 discloses methods of analyzing pore structures in a microporous polyolefin film. In one embodiment, a detectable material is applied to one surface of a microporous polyolefin film. The detectable material is capable of traveling through the pores in the film. The method includes focusing a confocal microscope at a depth within the film to obtain a first image of the detectable material within the pores of the film at the depth within the film. Three-dimensional images of the pore structure within a microporous polyolefin film include a plurality of aligned confocal microscope images, whereby each confocal microscope image includes a two-dimensional image of pore structure at a depth within the film.

U.S. Pat. No. 7,940,382 discloses a method for inspecting a defect of a hollow fiber porous membrane having substantially uniform, continuous inner hollow portions. In one embodiment, a part of a hollow fiber porous membrane is introduced into an irradiation chamber. The hollow fiber porous membrane is illuminated with light from the outside of the irradiation chamber, and the light exiting the hollow fiber porous membrane is detected on the outside of the irradiation chamber.

U.S. Patent Application Publication No. US 2010/0259748 discloses a method of inspecting resin-coated films for defects. In one embodiment, a resin solution is applied on a surface of a film to provide a resin-coated film. An inspection light having a wavelength of about 385-415 nm is used to irradiate the resin-coated film to uncover any defects.

WO 2016/102938 discloses a method of measuring properties of a moving porous film such as the thickness, porosity and density of the film. The method uses measurements of the transmissivity of the porous film at a plurality of IR wavelengths at which the film exhibits substantially no absorption. The method provides a measurement related to scattering. From the measurement related to scattering, the parameters of the porous film may be directly or indirectly determined.

In spite of the above advances, there remains a need for systems and methods for inspecting and evaluating the integrity of components used to make sterile, medical device packages. In particular, there remains a need for systems and methods that identify and locate the presence of defects (e.g., pinholes) in the components that are used to make sterile, medical device packages. In addition, there remains a need for systems and methods for validating the integrity of medical device packages that use porous sheet components (e.g., TYVEK® sheets).

SUMMARY OF THE INVENTION

In one embodiment, a method of detecting defects (e.g., pinholes, tears) in a substrate used to make medical device packages preferably includes coating a substrate with a UV absorbent layer, and shining UV light onto or through the substrate having the UV absorbent coating. When a defect in the substrate is present, the UV light that passes through the defect in the substrate is detected by a UV sensor or UV camera for indicating the presence of a defect.

In one embodiment, a method of evaluating the integrity of a substrate used for medical device packaging preferably includes applying a UV absorbent layer over a surface of a substrate, placing the substrate over a UV reflective surface, directing UV light toward the substrate and the UV reflective surface, and detecting with a camera any UV light that is reflected from the surface of the substrate.

In one embodiment, the substrate may be porous or non-porous. In one embodiment, the substrate may be flexible. The substrate may be made of various materials including synthetic fibers, polyethylene fibers, flashspun high-density polyethylene fibers (e.g., TYVEK®), polymers, paper, and/or foil and combinations thereof.

In one embodiment, the UV absorbent layer that is applied to the substrate preferably absorbs light in a spectrum that matches the wavelength of the UV light directed toward the substrate.

In one embodiment, the UV absorbent layer is transparent in light in the visible spectrum. As a result, when the substrate is in visible light, any printing or label that is applied to a substrate may be viewed through the transparent, UV absorbent layer that is applied to the substrate.

In one embodiment, a package substrate may have a first major surface and a second major surface. In one embodiment, the UV absorbent layer is applied over the first major surface of a substrate. In one embodiment, the UV absorbent layer is applied over the second major surface of a substrate. In one embodiment, the UV absorbent coating may be applied over both the first and second major surfaces of a substrate.

In one embodiment, the camera is sensitive to UV light for detecting any UV light that is reflected from the substrate having the UV absorbent layer.

In one embodiment, a method may include providing an optical filter in the optical path of the camera. In one embodiment, the optical filter is configured to transmit the reflected UV light to the camera and block or filter out visible and infrared light from reaching the camera.

In one embodiment, a method of inspecting a substrate preferably includes displaying images of the reflected UV light on a visual display screen. In one embodiment, defects in a substrate are displayed as specks of light on the visual display screen.

In one embodiment, a package substrate is rejected if the reflected UV light detected by the camera indicates that the substrate has at least one opening having a size that is greater than or equal to a predetermined size, such as a size being greater than or equal to 10 microns.

In one embodiment, a package substrate is accepted if the reflected UV light detected by the camera indicates that the substrate has no openings that are greater than or equal to a predetermined size, such as 10 microns.

In one embodiment, a method of evaluating the integrity of a substrate used in medical device packaging preferably includes providing a flexible, porous substrate having a first major surface, and a second major surface, applying a UV absorbent layer over at least one of the first and second major surfaces of the flexible, porous substrate, and placing the flexible, porous substrate over a UV reflective surface, such as a UV reflective film.

In one embodiment, a method preferably includes directing UV light toward the flexible, porous substrate and the UV reflective surface, whereby the UV absorbent layer absorbs light in a spectrum that matches the wavelength of the UV light, and detecting with a UV sensitive camera any UV light that is reflected from the first and second surfaces of the flexible, porous substrate.

In one embodiment, a method desirably includes displaying images of the reflected UV light that is detected by the UV sensitive camera on a visual display screen.

In one embodiment, a method may include rejecting the flexible, porous substrate if the reflected UV light that is detected by the UV sensitive camera indicates that the flexible, porous substrate has at least one opening having a size that is greater than or equal to 10 microns.

In one embodiment, a method may include accepting the flexible, porous substrate if the reflected UV light detected by the camera indicates that the flexible, porous substrate has no openings that are greater than or equal to 10 microns.

In one embodiment, a method desirably includes positioning an optical filter in the optical path of the UV sensitive camera. In one embodiment, the optical filter is configured to transmit the reflected UV light to the UV sensitive camera and block visible and infrared light from reaching the UV sensitive camera.

In one embodiment, a method of evaluating the integrity of a substrate used in medical device packaging preferably includes applying a UV absorbent layer over a major surface of a substrate, directing UV light toward the substrate, detecting with a UV sensitive camera any UV light that is reflected from the major surface of the substrate, and rejecting the substrate if the reflected UV light detected by the UV sensitive camera indicates that the substrate has at least one opening having a size that is greater than or equal to 10 microns.

In one embodiment, the substrate may be made of synthetic fibers, polyethylene fibers, flashspun high-density polyethylene fibers, paper, foil, polymers, and/or thermoformed polymers and combinations thereof.

In one embodiment, the UV sensitive camera is configured to detect light within the ultraviolet light spectrum and block light within the visible and infrared light spectrums.

In one embodiment, the substrate may include a container such as a thermoformed container. In one embodiment, the thermoformed container may be a tube or a polymer container. In one embodiment, the container may have a container opening that is adapted to receive a medical device (e.g., sutures, surgical tool, surgical mesh). In one embodiment, a flexible substrate may be sealed over the container opening of the container. The flexible substrate may have a UV absorbent coating. An inspection method may include using UV absorbent coatings to inspect for defects in either the container and/or the flexible substrate that seals the container opening.

In one embodiment, a system for evaluating the integrity of a substrate used in medical device packaging preferably includes at least one UV light source that generates UV light having a wavelength that lies within the UV light spectrum, and a UV absorbent material that absorbs light that matches the wavelength of the UV light generated by the UV light source. The UV absorbent material may be applied to a substrate.

In one embodiment, the system may include a UV reflective surface that is adapted to reflect the UV light generated by the UV light source, and a UV sensitive camera that is configured to detect reflected UV light that is not absorbed by the UV absorbent material and block light within visible and infrared light spectrums.

In one embodiment, the system may include a monitor and/or a visual display for displaying images of the reflected UV light that is detected by the UV sensitive camera.

In one embodiment, the system may include an optical filter that is placed within the optical path of the UV sensitive camera. In one embodiment, the optical filter is configured to transmit the reflected UV light to the UV sensitive camera and block or filter out visible and infrared light from reaching the UV sensitive camera.

In one embodiment, the system may be used to test substrates used to make sterile, medical device packages. In one embodiment, a substrate may have a first major surface with the UV absorbent material overlying the first major surface of the substrate. In one embodiment, the substrate may be disposed between the UV sensitive camera and the UV reflective surface.

In one embodiment, a flexible substrate is coated on at least one side with a UV absorbent material that will absorb UV radiation in the same wavelength spectrum as UV light generated by a UV light source. The UV light source may be one or more standalone sources or constructed into a fixture (e.g., a light box). The UV wavelength spectrums may include Long Wave (UV-A) at 320-400 nm, Medium Wave (UV-B) at 280-320 nm, and/or Short Wave (UV-C) at 200-280 nm.

In one embodiment, the UV light source is directed at the flexible substrate coated with the UV absorbent material from either above the substrate, below the substrate, or both above and below the substrate. The side of the flexible substrate coated with the UV absorbent layer may face toward or away from the UV light source and/or a camera system.

In one embodiment, the presence of the UV radiation is enough, and the exact angle of the radiation or coated material is not a determining factor. When testing the flexible substrate, the material coated with the UV absorbent layer may be left sealed or maintained separate from a package. In one embodiment, a backing material that reflects UV light, such as a UV reflective film, may be used to enhance the detection capabilities of a detection system or method.

In one embodiment, a detection system preferably includes a camera equipped with a sensor capable of receiving UV radiation. The system may include an optical filter that is in the optical path of the camera that allows UV light to pass therethrough while blocking visible and infrared light.

In one embodiment, a system may include an optical filter such as a UV transmission filter that operates in the same UV wavelength spectrum as the UV light source. The optical filter is preferably within the optical path of the camera and preferably lies between the substrate and the camera.

In one embodiment, the UV transmission filter allows UV light and/or UV radiation to pass through the filter and into the camera sensor. In one embodiment, the optical filter preferably absorbs or blocks all visible and infrared light.

In one embodiment, the camera is capable of converting the UV light exposure to an image output. In one embodiment, the image output preferably shows a contrast between areas of the substrate that have the UV absorbent coating and areas of the substrate without the UV absorbent coating. In one embodiment, the areas of the substrate without the UV coating indicate the presence of defects (e.g., pinholes, tears) in the substrate, which allows a user to quickly identify breaches in the integrity of the substrate material.

In one embodiment, a method for detecting defects in a substrate, such as a film or foil substrate, includes coating a top surface of the substrate with a UV (ultraviolet light) absorbent coating, placing a UV reflective film opposite a bottom surface of the substrate, directing a source of UV light at the top surface of the substrate, and detecting with a UV sensitive camera the UV light that is reflected from the top side of the substrate, thus identifying and detecting pinholes in the substrate.

In one embodiment, a method of detecting defects (e.g., pinholes) in a thin substrate such as a film or a foil having a top side and bottom side preferably includes coating the top side and/or the bottom side of the substrate with a UV (ultraviolet light) absorbent coating, directing a source of UV light at the bottom side of the substrate, and detecting with a UV sensitive camera the UV light that is transmitted through the substrate, thus identifying and detecting defects in the substrate.

In one embodiment, the UV absorbent coating is transparent in visible light, thereby enabling printing or labels to be placed on the substrate that remains visible through the transparent UV absorbent coating.

In one embodiment, the package sterile barrier may include either a porous or a non-porous material (i.e., TYVEK®, paper, foil).

In one embodiment, the UV light source preferably directs the light at the substrate along an axis that is perpendicular to the substrate (i.e., at an angle of zero (0) degrees to a major face of the substrate). In one embodiment, the UV light source preferably directs light at the substrate at an angle between about 0-60 degrees from a defect in the substrate in order to make allow the UV light to pass through the defect and/or the substrate. In one embodiment, two or more UV light sources may be provided to insure that the UV light passes through any defects present in the substrate.

In one embodiment, an optical filter may be an absorptive filter made from glass to which various inorganic or organic compounds have been added. The inorganic or organic compounds preferably absorb some wavelengths of light (e.g., visible and infrared light) while transmitting others (e.g., ultraviolet light). The inorganic or organic compounds may also be added to a plastic lens (often polycarbonate or acrylic) to produce optical filters that are lighter and cheaper than glass filters.

These and other preferred embodiments of the present invention will be described in more detail below.

BRIEF DESCRIPTION OF THE DRAWINGS

FIG. 1B-1 shows a top view of the substrate shown in FIG. 1B.

FIG. 12C-1 shows a magnified view of a section of the substrate shown in FIG. 12C.

DETAILED DESCRIPTION OF PREFERRED EMBODIMENTS

Figure 1A:
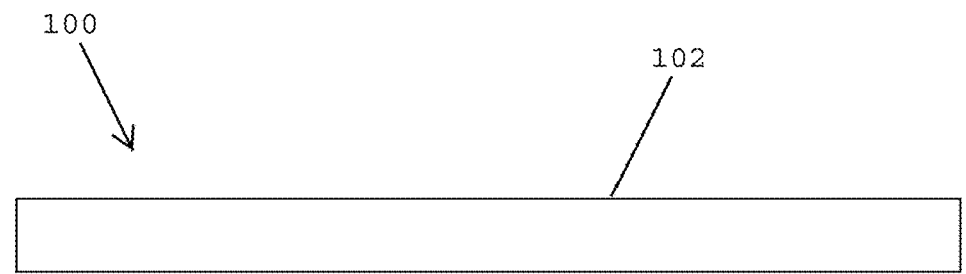
FIG. 1A shows a substrate used for medical device packaging, in accordance with one embodiment of the present patent application.

Referring to FIG. 1A, in one embodiment, a substrate 100 preferably includes a first major surface 102 and a second major surface 104. In one embodiment, the substrate 100 may be utilized as a sterile barrier in a medical device package. In one embodiment, the substrate 100 may be either porous or non-porous. In one embodiment, the substrate 100 may be utilized for packaging medical devices such as sutures, surgical tools and surgical meshes. In one embodiment, the substrate may be made of a synthetic material, such as the polyethylene fibrous material sold under the trademark TYVEK® by DuPont of Wilmington, Del., or other materials such as paper, and/or foil.

Medical device packages (e.g., pouches) made of TYVEK® are used by medical device and pharmaceutical manufacturers for packaging a wide variety of sterilized medical devices. Packages and sterilization pouches made of TYVEK® are used in hospitals and other healthcare settings for in-house sterilization of surgical instruments. See http://www.dupont.com/products-and-services/packaging-materials-solutions/pharmaceutical-packaging/brands/tyvek-sterile-packaging/uses-and-applications/protective-clean-peel-pouches.html TYVEK® sheets provide outstanding resistance to microbial penetration, helping to maintain sterility of the contents of packages or pouches until they are opened. TYVEK® sheets are typically made of high-density polyethylene (HDPE). TYVEK® sheets are extremely stable when exposed to sterilizing gases and high-energy sterilization processes. TYVEK® sheets are compatible with all of the most commonly used sterilization methods, including ethylene oxide (EO), gamma, electron-beam, steam and low-temperature oxidative sterilization processes. Id.

One advantage of using TYVEK® sheets for medical device packages and sterilization pouches is its superior tear strength and puncture resistance compared to medical-grade papers. TYVEK® sheets are tough and resist punctures. Id. In one embodiment, the present patent application discloses systems and methods for evaluating TYVEK® sheets, which are used to assemble sterile, medical device packages, for defects (e.g., pinholes).

Medical device packages are designed to keep bacteria and contaminants from entering a sterile, sealed region that contains a medical device. A defect, such as a hole or an opening, in a medical device package may allow bacteria to enter into the sterile, sealed region of the package. This is undesirable because the medical device in the package may become contaminated. When a hole or opening (i.e., a defect) is created in a medical device package, bacteria requires a carrier (e.g., fluid, pressure) to pass through the hole or opening and into the sterile, sealed region of the package. The probability of bacteria being exposed to a carrier and then finding a hole smaller than 10 microns to enter the sterile region of the package is incredibly small. Thus, in one embodiment, a detected opening in a substrate may be considered to be a defect in the substrate if the opening is greater than or equal to 10 microns. In one embodiment, a detected opening in a substrate of less than 10 microns would not be considered to be a defect because it is extremely unlikely that bacteria would pass through the opening.

Figure 1B:
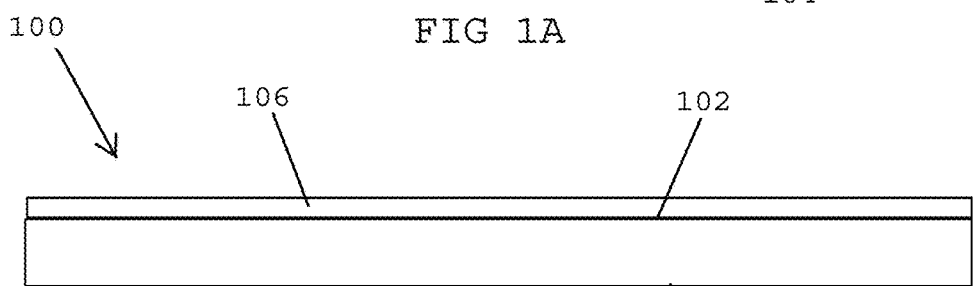
FIG. 1B shows the substrate of FIG. 1A with a UV absorbent layer covering a first major surface of the substrate, in accordance with one embodiment of the present patent application.

Referring to FIG. 1B, in one embodiment, a layer of a UV absorbent material 106 is applied over the first major surface 102 of the substrate 100. In one embodiment, the UV absorbent layer 106 is adapted to absorb UV light that is directed at the first major surface 102 of the substrate 100. In one embodiment, a second UV absorbent layer may be applied over the second major surface 104 of the substrate 100. In one embodiment, a first UV absorbent layer may be applied over the first major surface and a second UV absorbent layer may be applied over the second major surface of the substrate.

Figures 1, 1B:
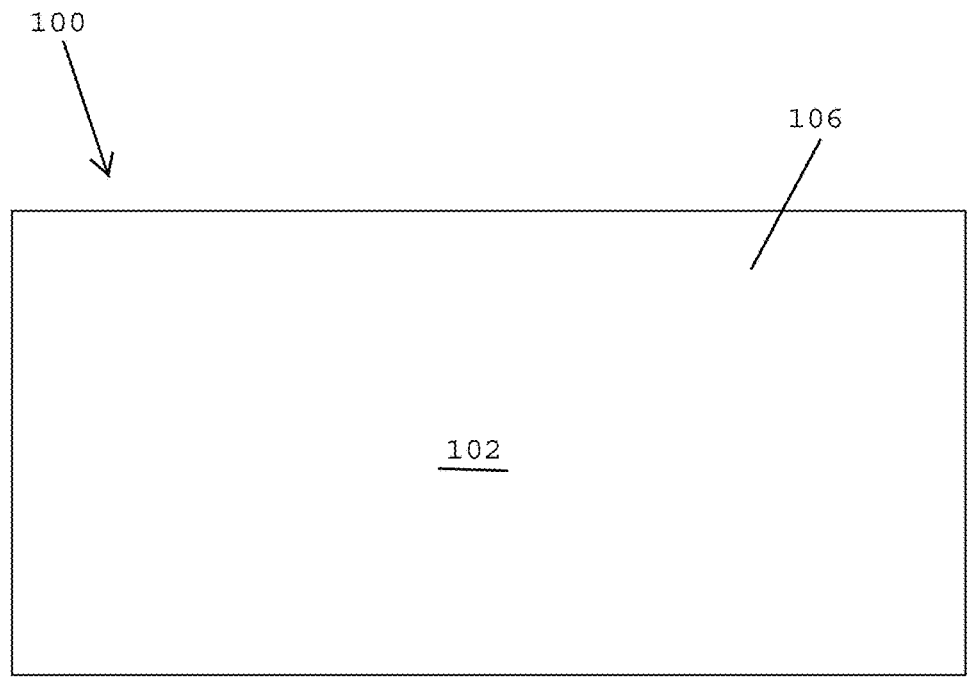

FIG. 1B-1 shows a top view of the substrate shown in FIG. 1B. The first major surface 102 of the substrate 100 is covered by the UV absorbent layer 106 (FIG. 1B). In one embodiment, the UV absorbent layer may be transparent so that indicia (e.g. printing, a label) provided over the first major surface 102 of the substrate 100 may be visible (when in visible light) through the transparent UV absorbent layer 106 (FIG. 1B).

Figure 2:
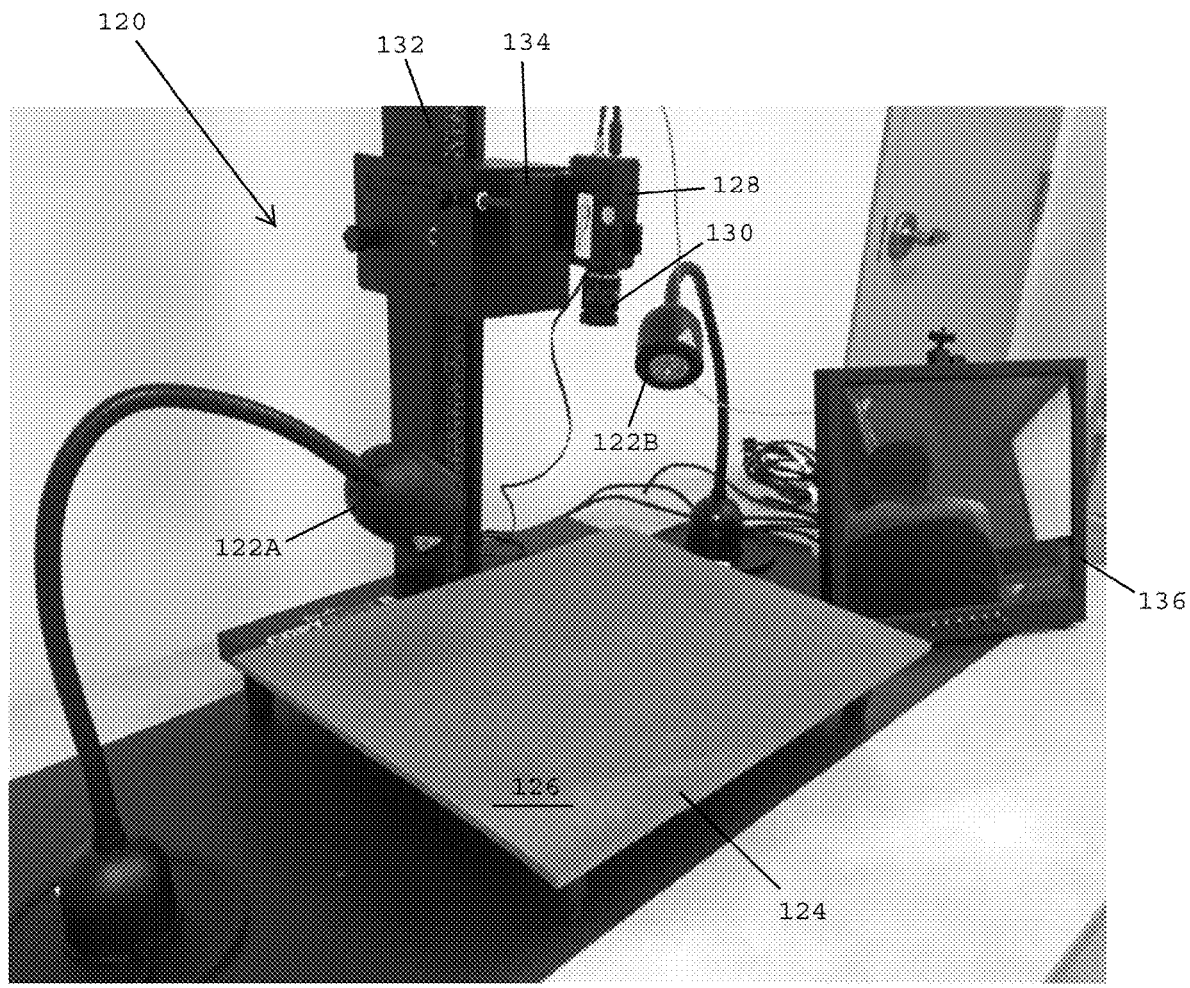
FIG. 2 shows a perspective view of a system for detecting defects in a substrate, in accordance with one embodiment of the present patent application.

Referring to FIG. 2, in one embodiment, a system 102 is utilized for detecting defects in a substrate. The presence of defects is undesirable because bacteria and contaminants may infiltrate a package through the defect(s). In one embodiment, the defects may include tears, rips, openings, and/or pinholes that are present in a substrate. In one embodiment, the system 120 for detecting defects desirably includes UV light sources 122A, 122B that are adapted to generate UV light. The UV light is preferably directed toward a substrate having one or more UV absorbent layers. The UV light may be directed at a topside or an underside of a substrate. In one embodiment, the UV light sources 122A, 122B generate UV light having a wavelength in the ultraviolet range of between about 10-400 nm and more preferably about 200-400 nm. In one embodiment, the system 120 for detecting defects desirably includes a UV reflective substrate 124 having a top surface 126 that opposes the UV light sources 122A, 122B. In one embodiment, the UV reflective substrate 124 is adapted to reflect the light generated by the UV light sources 122A, 122B.

In one embodiment, the system 120 for detecting defects preferably includes a camera 128 that is configured to detect UV light. In one embodiment, the camera 128 is configured to detect and/or sense only UV light and not detect light that is in the visible or infrared spectrum. In one embodiment, the camera 128 may include an optical filter 130 that transmits UV light and blocks or filters out light in the visible and infrared spectrums so that the UV camera 128 only receives light in the UV light spectrum.

In one embodiment, the system 120 may include a column 132, such as a vertical support column, having a camera mount 134 coupled therewith. In one embodiment, the camera 128 is connected with the camera mount 134. In one embodiment, the camera mount 134 is configured to move up and down the column 132 for adjusting the distance between the camera 128 and the top surface 126 of the UV reflective substrate 124. In one embodiment, the distance between the camera 128 and the UV reflective substrate 126 may be adjustable for properly gauging the size of any defects or openings that are present in the substrate.

In one embodiment, the defect detection system 120 desirably includes a monitor 136 that is adapted to display images transmitted by the camera 128. The monitor 136 may display pictures, video, and/or moving pictures of the images captured and transmitted by the camera. In one embodiment, when a substrate having a UV absorbent layer is positioned over the top surface 126 of the UV reflective substrate 124, the images of the substrate captured by the camera 128 are displayed on the monitor 136.

Figure 3:
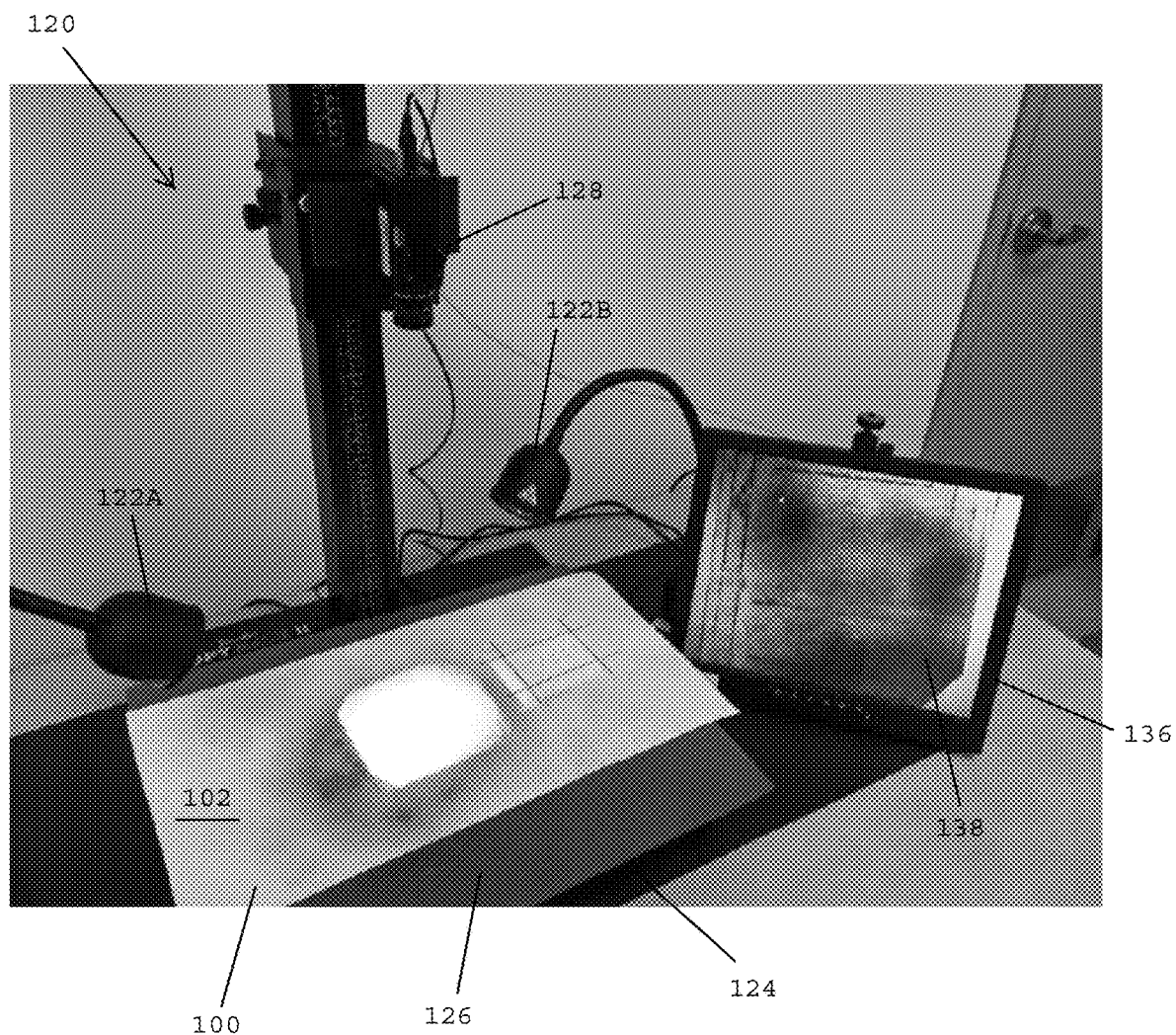
FIG. 3 shows the system of FIG. 2 being used for testing a substrate, in accordance with one embodiment of the present patent application.

Referring to FIG. 3, in one embodiment, the substrate 100 having the UV absorbent layer is positioned over the top surface 126 of the UV reflective substrate 124. The UV light sources 122A, 122B are turned on to direct UV light at the first major surface 102 of the substrate 100. As described above, the first major surface 102 of the substrate 100 is desirably covered by the UV absorbent layer 106 (FIG. 1B). If there are any defects such as openings or pinholes in the substrate 100, the UV light generated by the UV light sources 122A, 122B will reflect off the top surface 126 of the UV reflective substrate 124, pass through the defects, and be detected by the camera 128, which is configured to detect UV light. The UV light image 138 of the substrate 100 that is captured by the camera 128 is displayed on the monitor 136.

In one embodiment, a substrate such as TYVEK® has a pore size of about 0.22 microns. Bacteria has a size of about 0.3-60 microns. Thus, bacteria is incapable of passing through the pores of the TYVEK® substrate. The system disclosed herein will detect a defect, however, when the size of an opening in the TYVEK® substrate is large enough to allow bacteria to pass therethrough (e.g., when the opening is greater than or equal to 10 microns).

Figure 4:
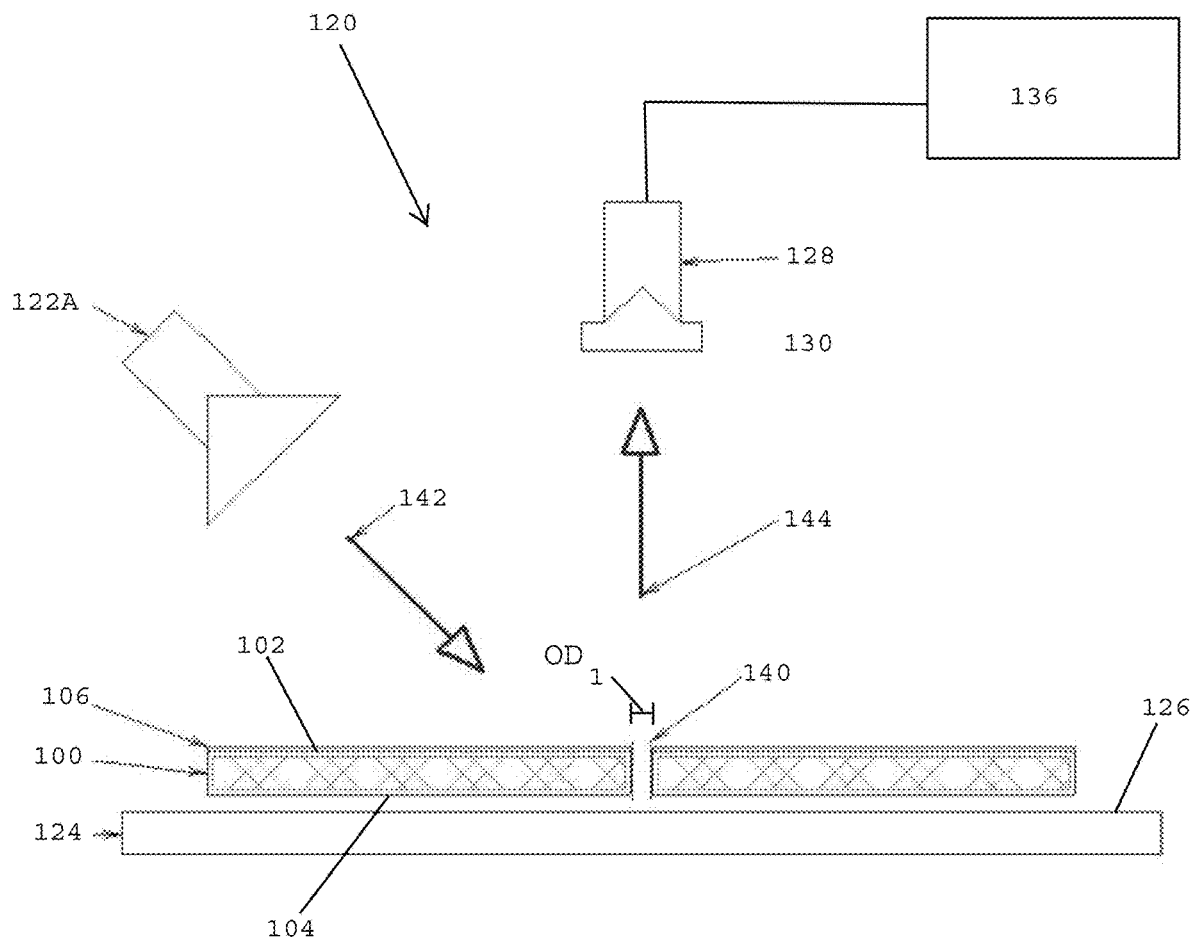
FIG. 4 shows a schematic view of the system shown in FIG. 3.

Referring to FIG. 4, in one embodiment, the defect detection system 120 includes the UV reflective substrate 124 having a top surface 126 that is adapted to reflect UV light. In one embodiment, the substrate 100 having the UV absorbent layer 106 covering the first major surface 102 of the substrate is positioned over the top surface 126 of the UV reflective substrate 124. In the embodiment shown in FIG. 4, the substrate 100 has a pinhole defect 140 that extends from the first major surface 102 to the second major surface 104 of the substrate 100. The pinhole defect 140 has an inner diameter $ID_1$ that is greater than or equal to 10 microns, which is large enough to allow bacteria to pass through the substrate 100.

In one embodiment, the UV light 142 that is generated by the UV light source 122A is directed at the first major surface 102 of the substrate 100. The UV absorbent layer 106 covering the first major surface 102 of the substrate absorbs the UV light 142 that strikes the UV absorbent layer 106. In one embodiment, the UV light 142 that passes through the pinhole defect 140 is reflected toward the camera by the top surface 126 of the UV reflective substrate 124. The reflected UV light 144 passes back through the pinhole defect 140 and toward the UV camera 128 for being detected by the UV camera 128 (having the optical filter 130). In one embodiment, the UV camera 128 detects only the UV light that is reflected by the UV reflective substrate 126. In one embodiment, the optical filter 130 desirably screens out any light that is within the visible or infrared spectrum so that only UV light is detected by the UV camera 128.

Figure 5A:
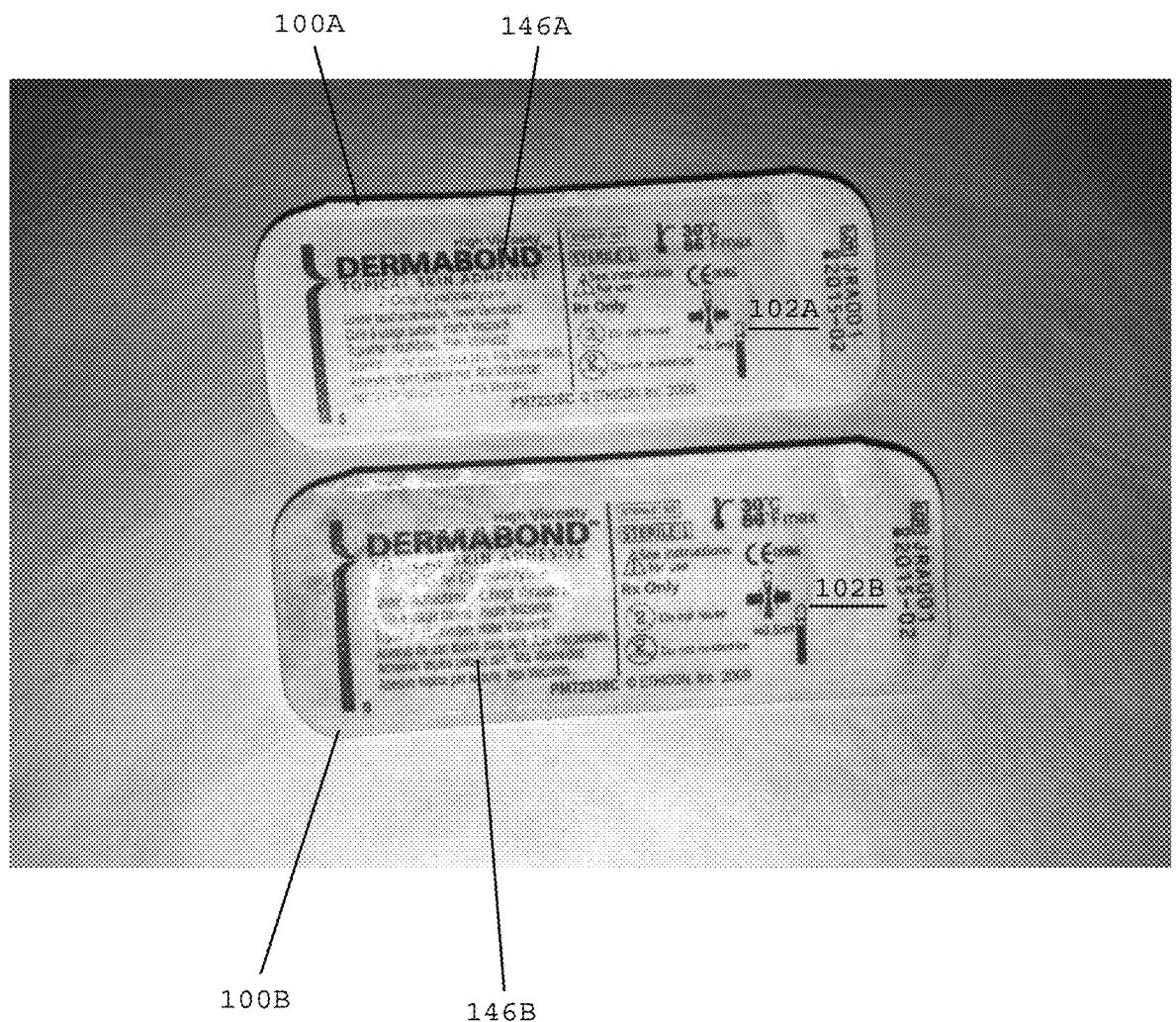
FIG. 5A shows a first substrate that is untreated and a second substrate that is covered with a UV absorbent layer, in accordance with one embodiment of the present patent application.

Referring to FIG. 5A, in one embodiment, a first substrate 100A for a first package has a first major surface 102A with indicia 146A printed on the first major surface for identifying the contents of the first package. The indicia 146A may include various information such as a product name and/or technical information related to using a device or product. The first major surface 102A of the first substrate 100A is not covered by a UV absorbent layer.

In one embodiment, a second substrate 100B for a second package has a first major surface 102B with indicia 146B printed on the first major surface for identifying the contents of a package, such as a medical device package. The indicia 146B may include various information such as a product name and/or technical information related to using a device or product. The first major surface 102B of the second substrate 100B is covered by a UV absorbent layer that is adapted to absorb light in the UV spectrum. The UV absorbent layer is preferably transparent to light in the visible spectrum so that the indicia printed on the second substrate 100B can be read in visible light.

In one embodiment, the first and second substrates 100A, 100B have microscopic pores formed therein that enable the contents of the packages to be sterilized while not allowing bacteria and/or contaminants to enter the respective packages. In one embodiment, the microscopic pores have a size of about 0.22 microns, respectively, which is smaller than the size of bacteria, thereby preventing the bacteria from entering the sterile zone of the packages.

Figure 5B:
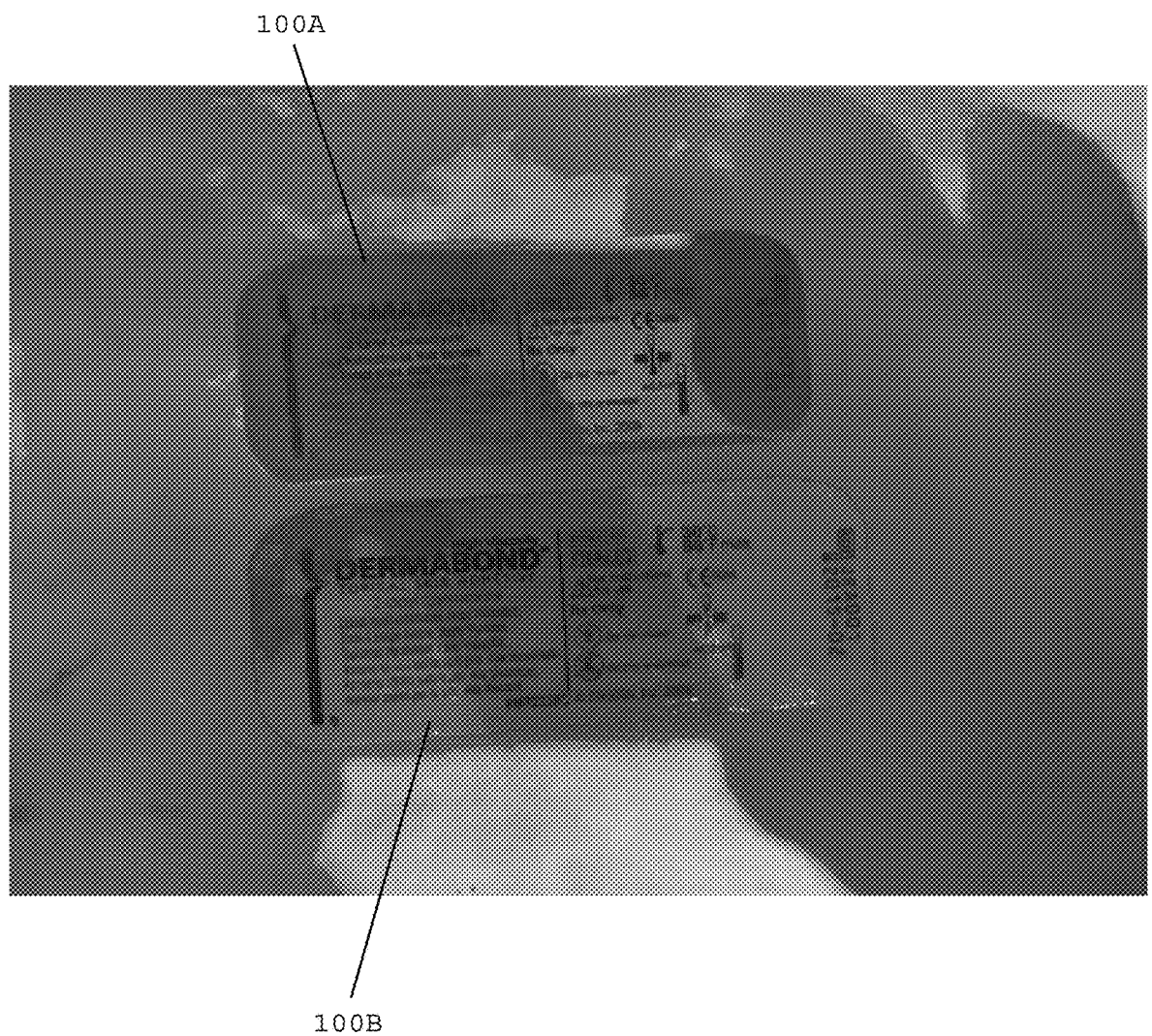
FIG. 5B shows the first and second substrates of FIG. 5A exposed to UV light.

FIG. 5B shows the first and second substrates 100A and 100B exposed to UV light. The optical filter is not being used with the camera so that visible light is also present in the image shown in FIG. 5B. Because the optical filter is not being used, the indicia 146A, 146B that is provided on the respective substrates 100A, 100B remains visible to the camera.

Figure 6A:
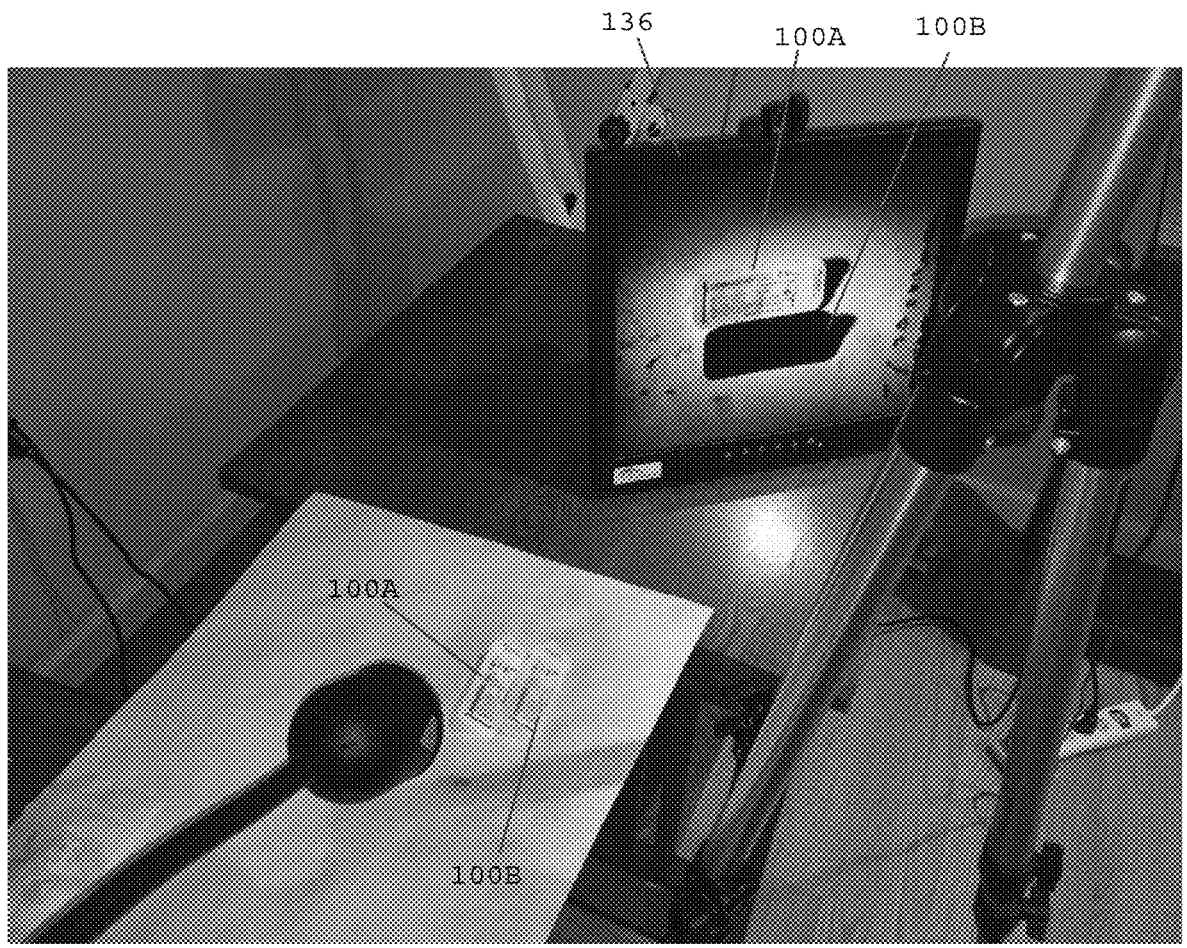
FIG. 6A shows a method of viewing the first and second substrates of FIG. 5B through a camera having an optical filter for display on a monitor, in accordance with one embodiment of the present patent application.
Figure 6B:
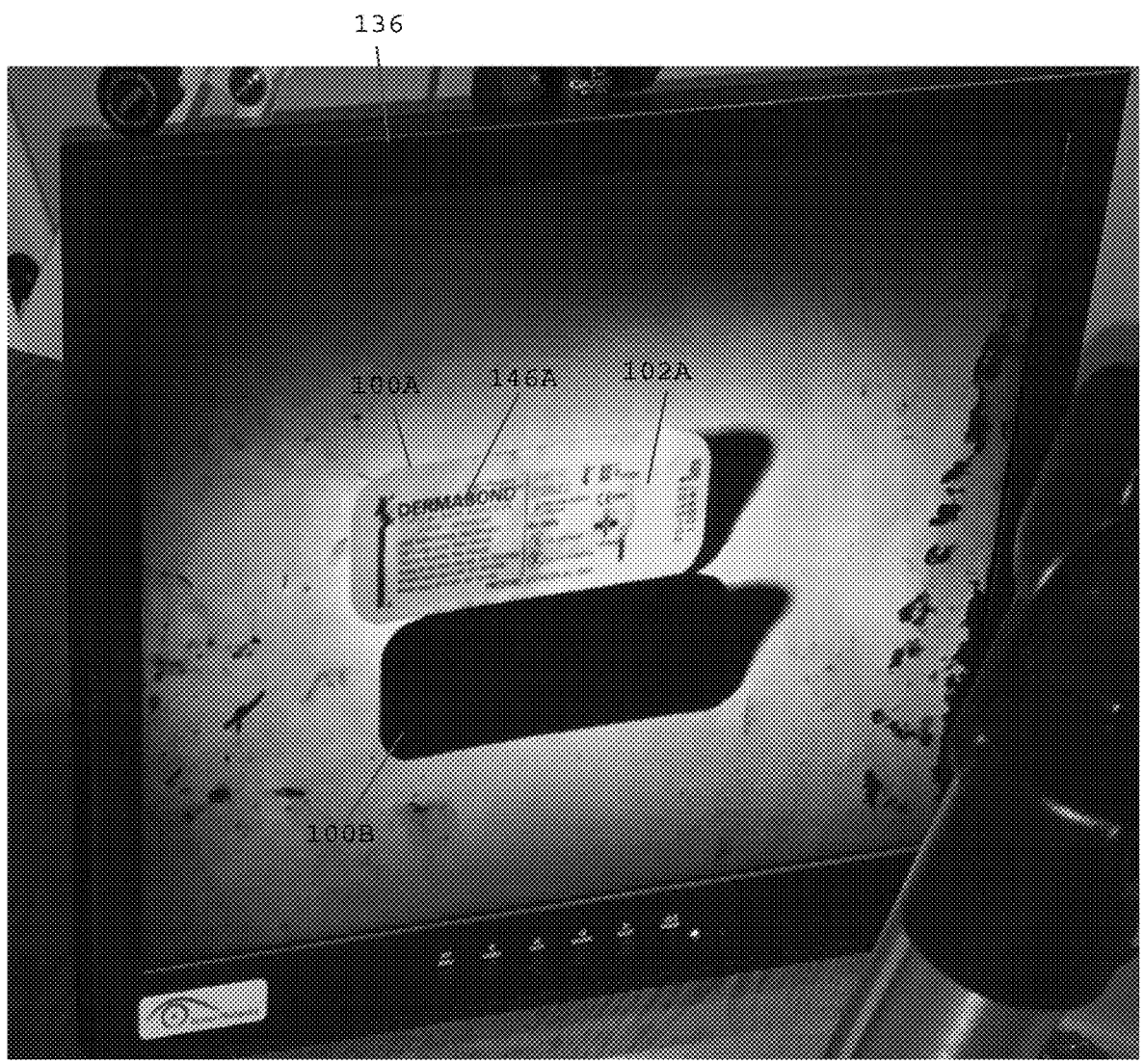
FIG. 6B shows a magnified view of the monitor shown in FIG. 6A.

Referring to FIGS. 6A and 6B, in one embodiment, when the optical filter 130 (FIG. 4) is used with the camera 128 (FIG. 4), the indicia 146A printed on the first major surface 102A of the first substrate 100A remains visible, while the indicia 146B (FIG. 5B) printed on the first major surface of the second substrate 100B is not visible. This is due to the fact that the optical filter blocks out visible light and the UV absorbent layer covering the second substrate 100B absorbs all of the UV light that strikes the UV absorbent layer on the second substrate. As a result, the second substrate 100B, covered by the transparent, UV absorbent layer, appears black on the monitor 136. In FIG. 6B, the second substrate 100B that is covered by a transparent, UV absorbent layer has no defects or openings so that the UV camera captures a completely black image for the second substrate 100B, which indicates that there are no defects present in the second substrate 100B. If pinhole defects were present in the second substrate, they would appear as specks of light on the monitor.

Figure 7:
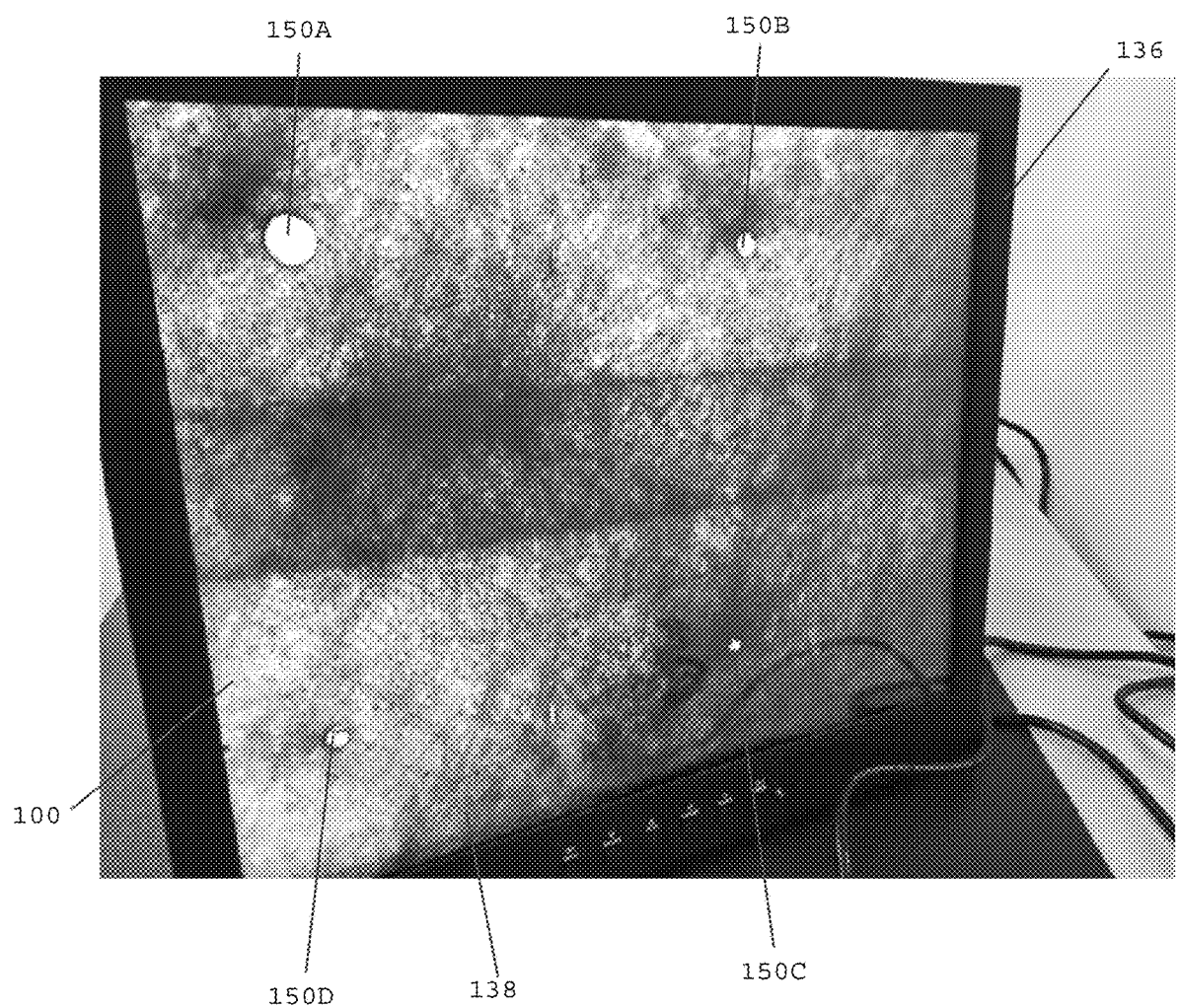
FIG. 7 shows a monitoring having an image of a substrate with pinhole defects present in the substrate, in accordance with one embodiment of the present patent application.

Referring to FIG. 7, in one embodiment, the images 138 captured by the UV camera 128 are displayed on the monitor 136. In FIG. 7, the UV camera has detected four openings 150A-150D present in the substrate 100. The openings 150A-150D are detectable by the UV camera because the UV light is not absorbed by the UV absorbent layer at the locations where the openings 150A-150D are present. As a result, the UV light that passes through the openings 150A-150D is reflected by the top surface 126 of the UV reflective substrate 124 (FIG. 4), passes back through the openings 150A-150D, and is captured by the UV camera 128. In instances where the substrate has no defects or openings, the UV absorbent layer absorbs all of the UV light so that the UV camera 128 does not detect any openings or defects in the substrate.

In FIG. 7, a first opening 150A is larger, a third opening 150C is smaller, and second and third openings 150B, 150D are intermediate in size. The second and third openings 150B, 150D are smaller than the first opening 150A and larger than the third opening 150C. In one embodiment, the first opening 150A is evaluated to be a defect in the substrate 100 because it is larger than 10 microns. In one embodiment, the third opening 150C is evaluated to not be a defect in the substrate 100 because it is smaller than 10 microns. In one embodiment, the second and third openings 150B, 150D are also considered to be defects in the substrate 100 because they have a size of about 10 microns. In one embodiment, the system for evaluating defects may include a central processing unit having one or more microprocessors and one or more software programs for automatically gauging the sizes of the openings in the substrate 100 that appear on the monitor 136. Thus, a system for evaluating the integrity of a package substrate may be automated and performed by a computer and software.

Figure 8:
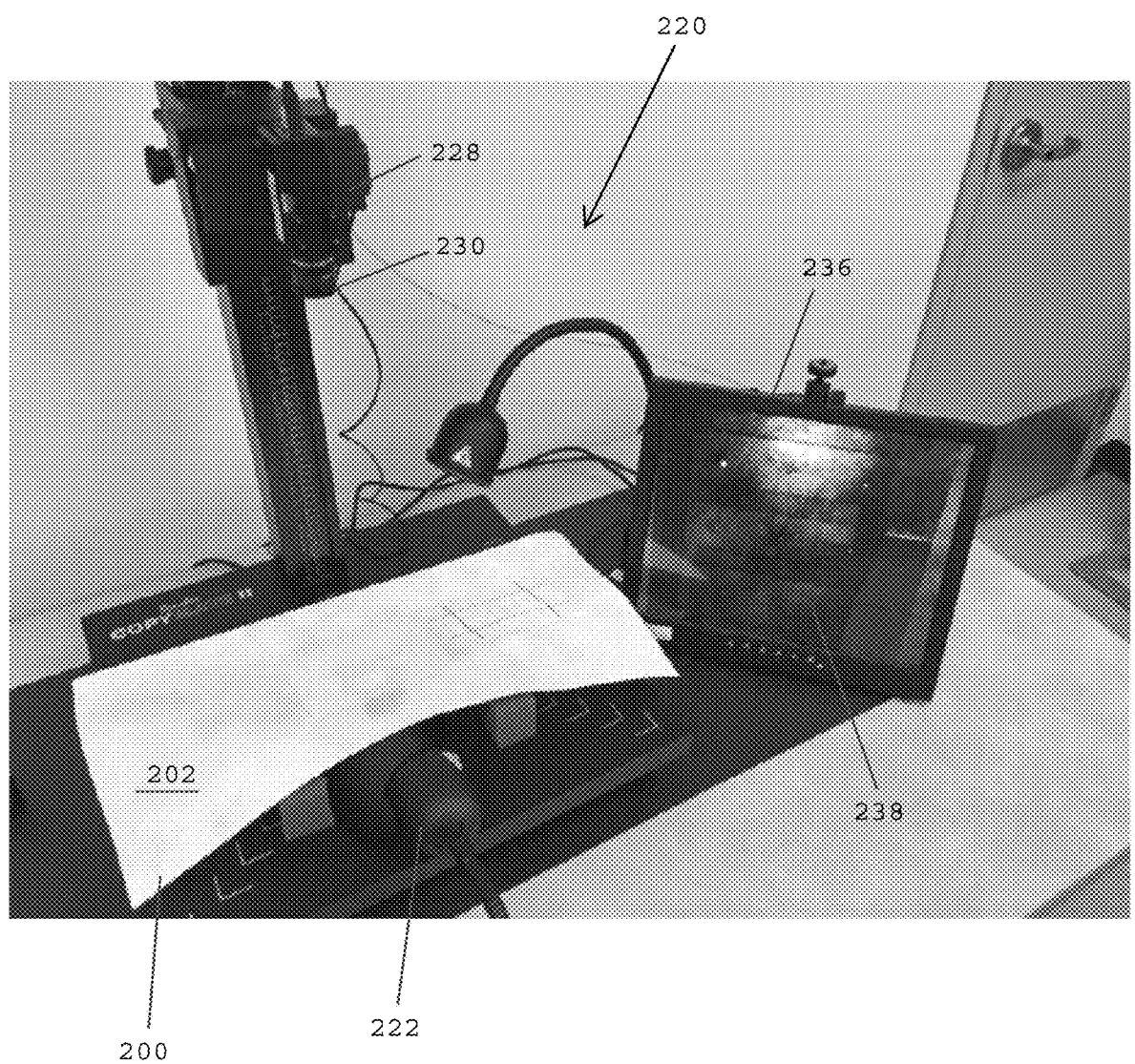
FIG. 8 shows a perspective view of a system for detecting defects in a substrate within UV illumination from beneath the substrate, in accordance with one embodiment of the present patent application.
Figure 9:
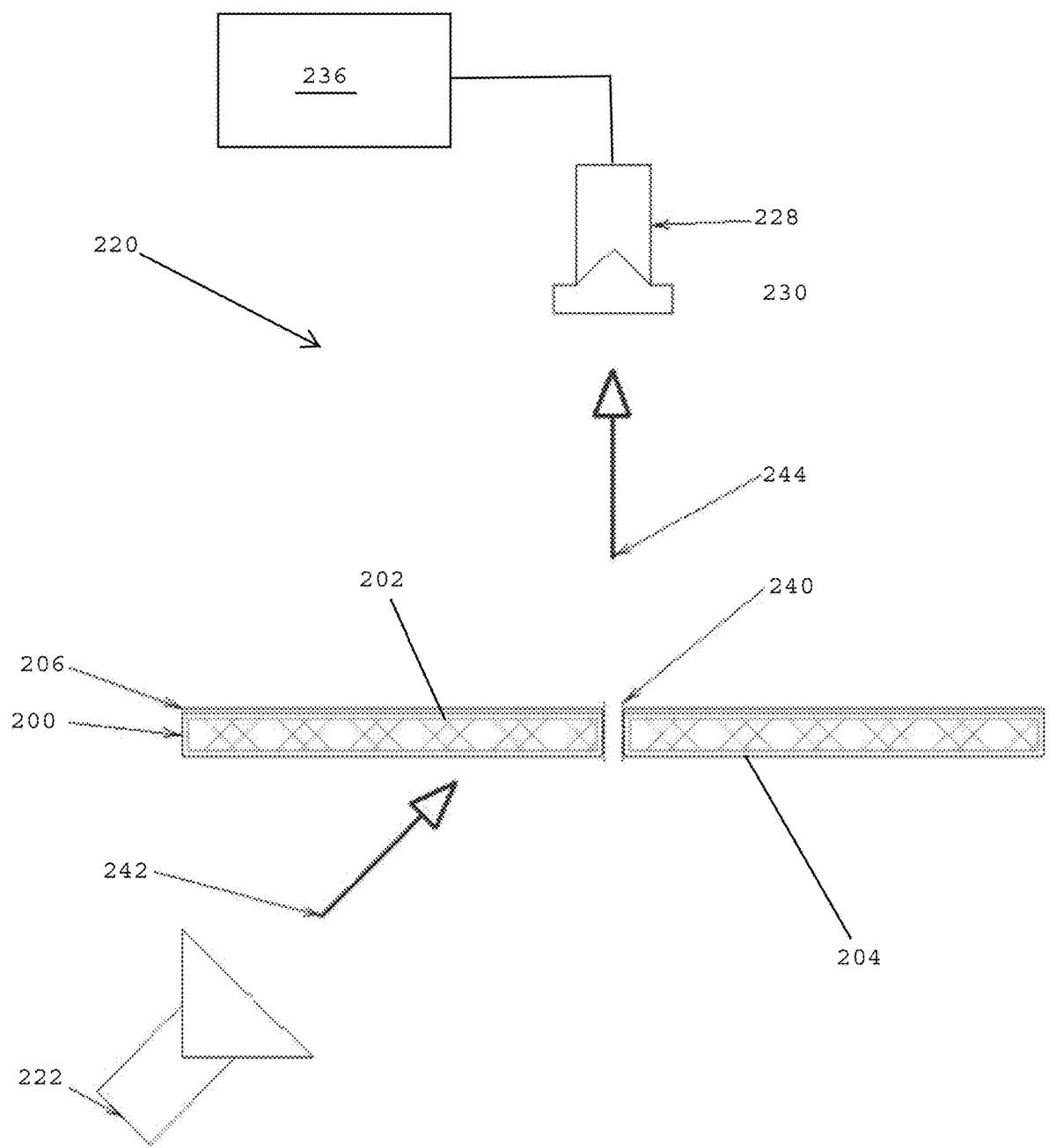
FIG. 9 shows a schematic view of the system shown in FIG. 8.

Referring to FIGS. 8 and 9, in one embodiment, a system 220 for detecting defects in a substrate preferably includes a substrate 200 having a first major surface 202 and a UV absorbent layer 206 covering the first major surface 202. The UV absorbent layer is preferably transparent so that visible light may pass through the UV absorbent layer.

In one embodiment, a UV light source 222 is directed at the second major surface 204 (i.e., the underside) of the substrate 200 so that the UV light 242 strikes the second major surface 204. The substrate 200 has a pinhole defect 240 (FIG. 9) that extends from the first major surface 202 to the second major surface 204. The UV absorbent layer 204 preferably absorbs the UV light 242 from the UV light source 222. However, some of the UV light is able to pass through the pinhole defect 240, as reflected UV light 244, so that it may be captured as an image by the UV camera 228, which is preferably covered by and/or coupled with the optical filter 230 that transmits UV light and blocks visible and infrared light. The UV camera 228 desirably transmits images of the substrate 200 to the monitor 236 for displaying images of the substrate 200 on the monitor. In one embodiment, the system 220 detects where the UV light is able to pass through the substrate, and the defects appear as specks of light in a visual display area of the monitor for identifying defects in the substrate. The specks of light that appear on the monitor preferably have the same size, shape, and location as the defects that are present on the substrate.

Figure 10A:
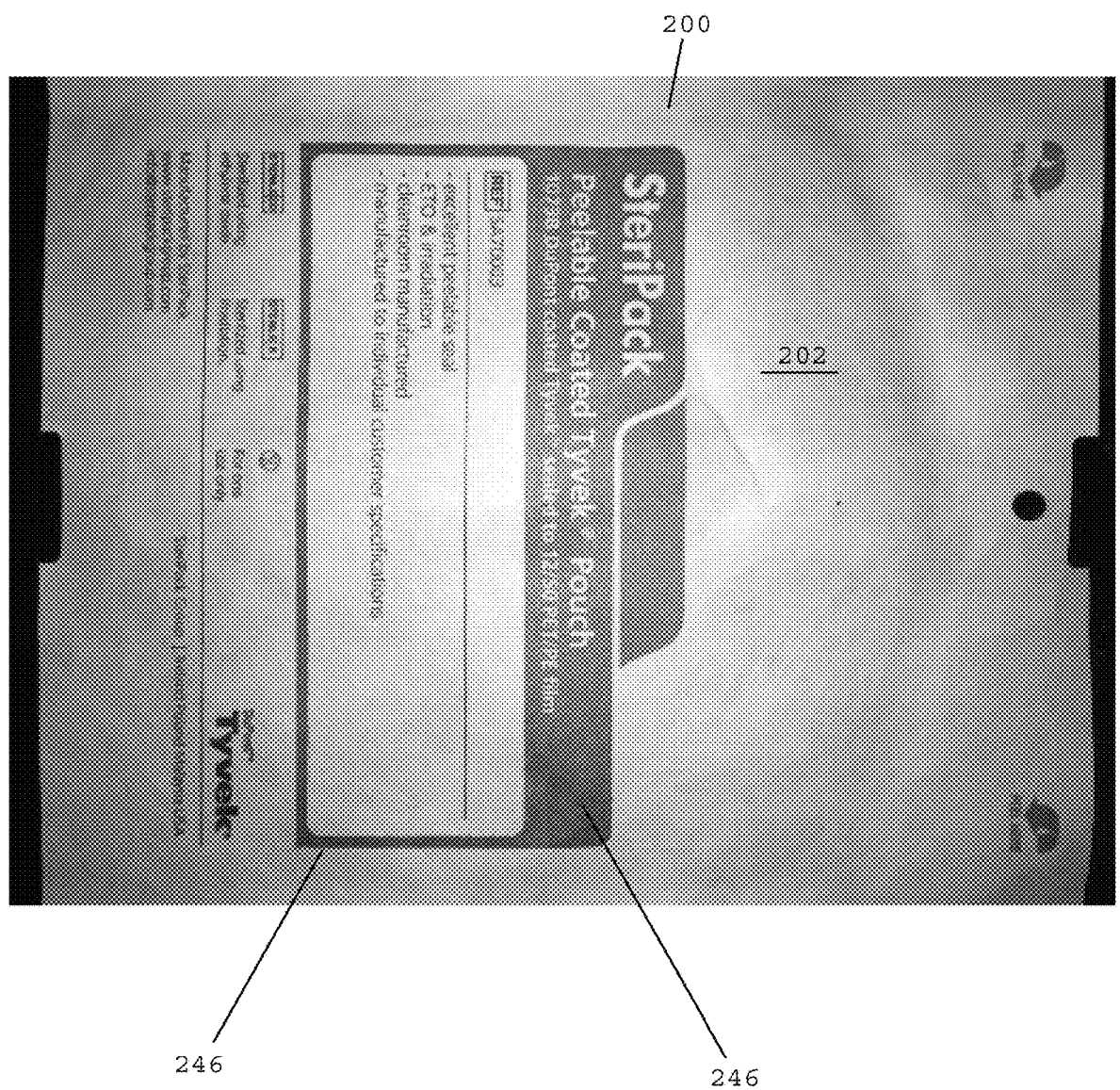
FIG. 10A shows a substrate that is covered with a UV absorbent layer, in accordance with one embodiment of the present patent application.

Referring to FIG. 10A, in one embodiment, a substrate 200 has a first major surface 202 with indicia 246 printed on the first major surface. A strip of a transparent, UV absorbent material is applied over the first major surface 202 of the substrate 200. The indicia 246 printed on the substrate remains visible through the transparent, UV absorbent layer.

Figure 10B:
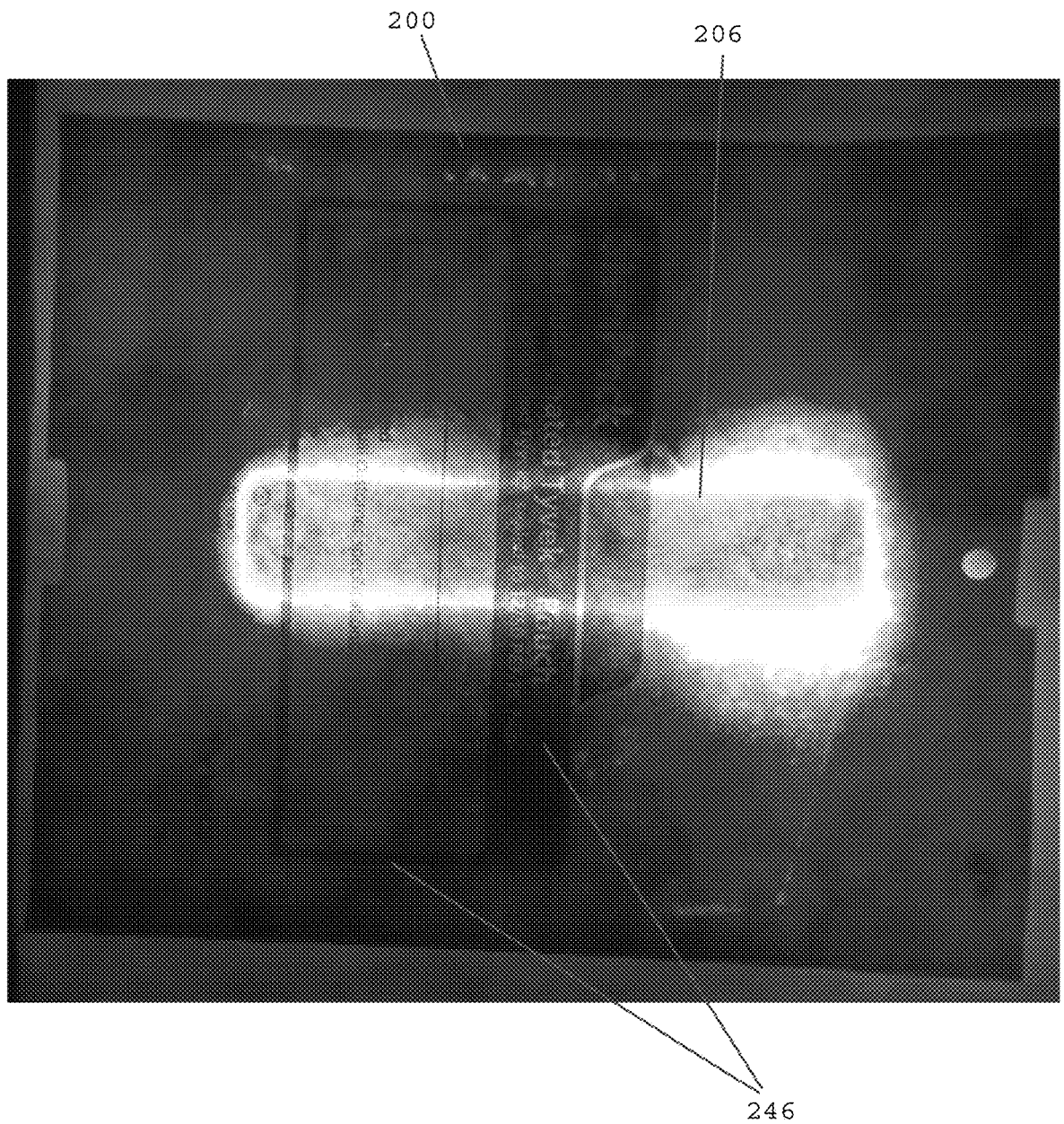
FIG. 10B shows the substrate of FIG. 10A exposed to UV light.
Figure 10C:
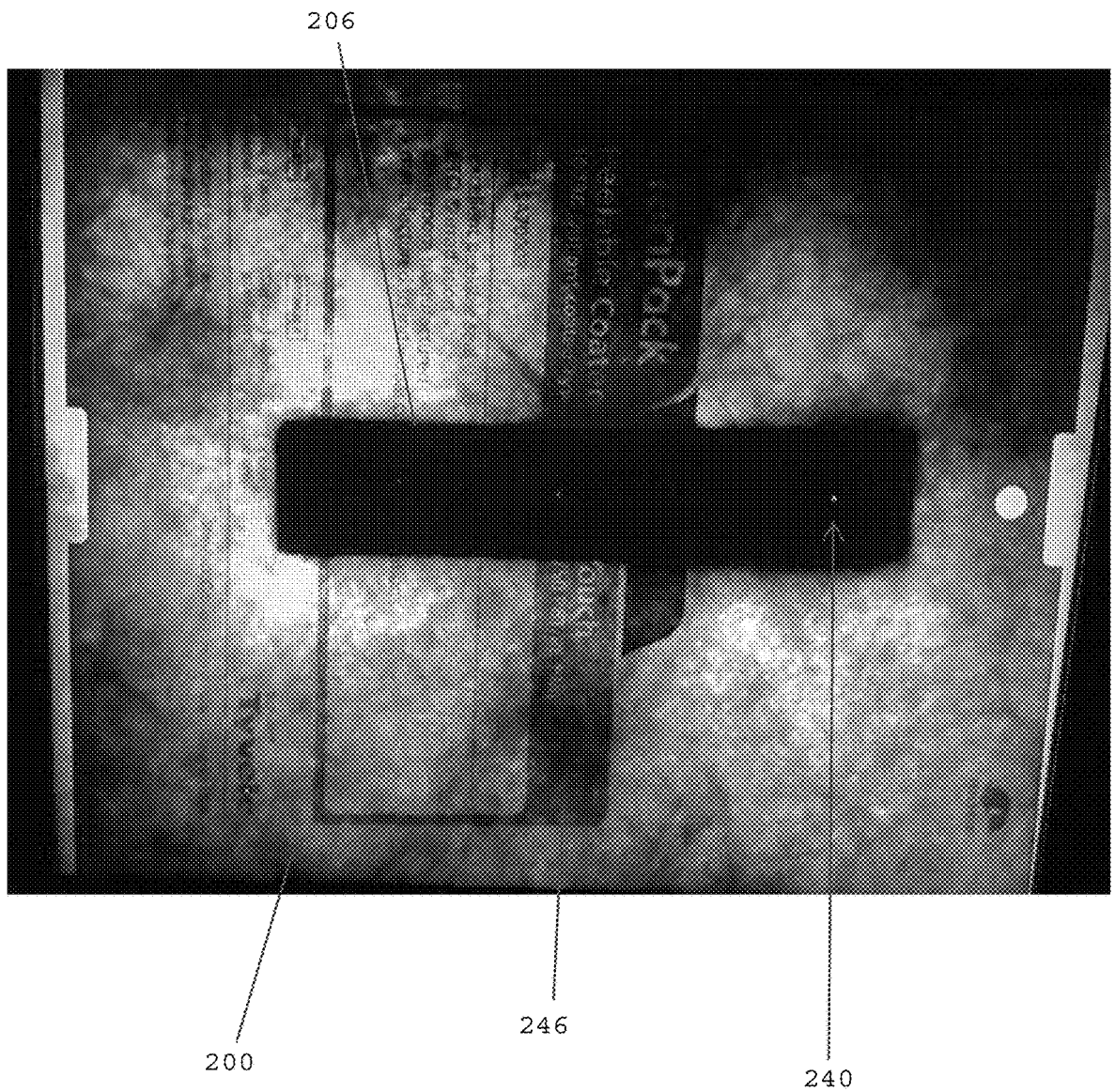
FIG. 10C shows a method of viewing the substrate of FIG. 10B through a camera having an optical filter for display on a monitor, in accordance with one embodiment of the present patent application.

Referring to FIG. 10B, in one embodiment, UV light is directed at the underside of the substrate. In FIG. 10B, the optical filter is not utilized so that the indicia printed on the first major surface of the substrate is captured by the UV camera. In FIG. 10C, the optical filter is used so that the UV absorbent layer 206 appears as a black strip when an image of the substrate is captured by the UV camera. Because the UV absorbent layer absorbs the UV light, the black strip 206 occludes the indicia 246 underlying the black strip. The UV camera captures an image of a pinhole defect 240 that is present in the substrate 200. The contrast between the black strip 206 and the white pinhole 240 highlights the location of the defect on the substrate.

Figure 11:
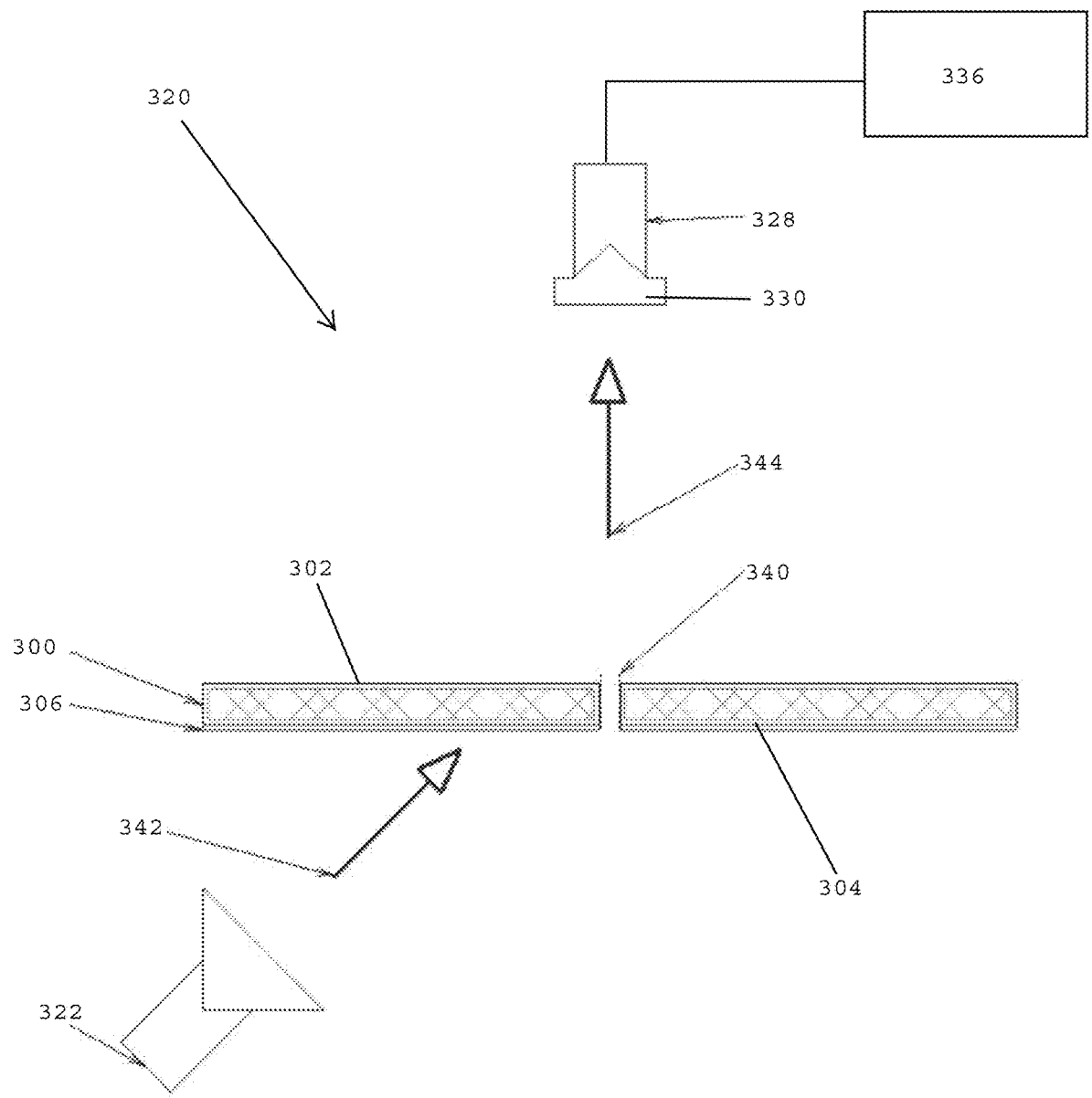
FIG. 11 shows a schematic view of a system for detecting defects in a substrate within UV illumination provided beneath the substrate, in accordance with one embodiment of the present patent application.

Referring to FIG. 11, in one embodiment, a substrate 300 has a first major surface 302 and a second major surface 304.

A UV absorbent layer 306 is applied over the second major surface 304. In one embodiment, a system 320 for detecting defects (e.g., pinholes) in the substrate 300 preferably includes a UV light source 322 that directs UV light 342 at the second major surface 304, which is covered by the UV absorbent layer 306. The UV absorbent layer absorbs the UV light 342 that impinges upon and/or strikes the UV absorbent layer 306. The substrate 300 has a defect in the form of a pinhole 340 that extends from the first major surface 302 to the second major surface 304. Because the UV absorbent layer is not present at the defect to absorb the UV light, the UV light 242 is able to pass through the pinhole defect 340. The camera 328 having the optical filter 330 is able to detect any reflected UV light 344 that passes through the pinhole defect 340 for identifying the presence of the pinhole 340 in the substrate 300. In one embodiment, images captured by the UV camera 328 are displayed on a monitor 336 as specks of light (e.g., white light) for identifying any defects that are present in the substrate 300.

Figure 12A:
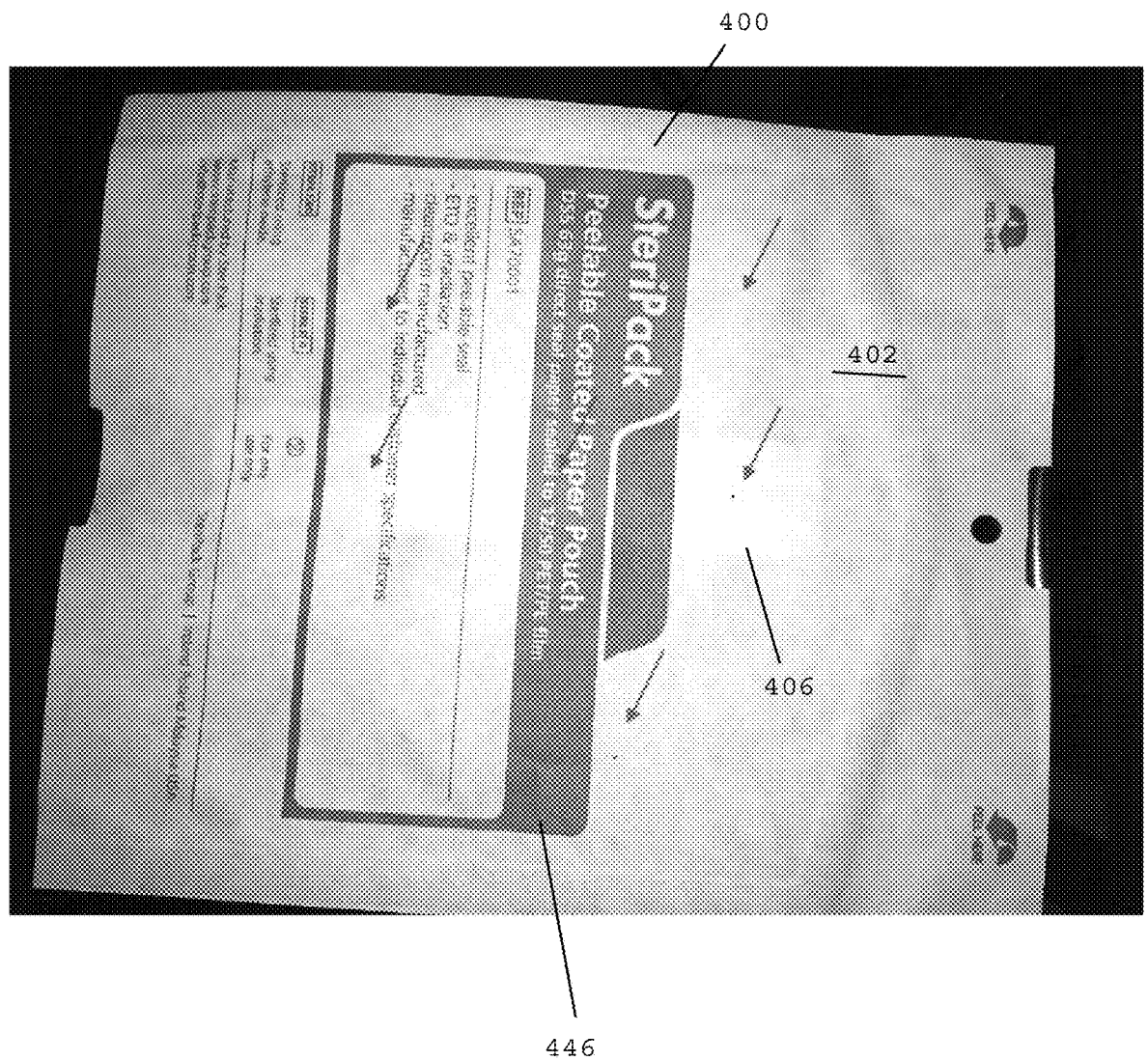
FIG. 12A shows a substrate that is covered with a UV absorbent layer, in accordance with one embodiment of the present patent application.

Referring to FIG. 12A, in one embodiment, the substrate 400 for a medical device package preferably has a first major surface 402 with indicia 446 printed on the first major surface. A strip of a transparent, UV absorbent material 406 is applied over the first major surface 402 of the substrate 400. The substrate has pinhole defects that are highlighted by arrows.

Figure 12B:
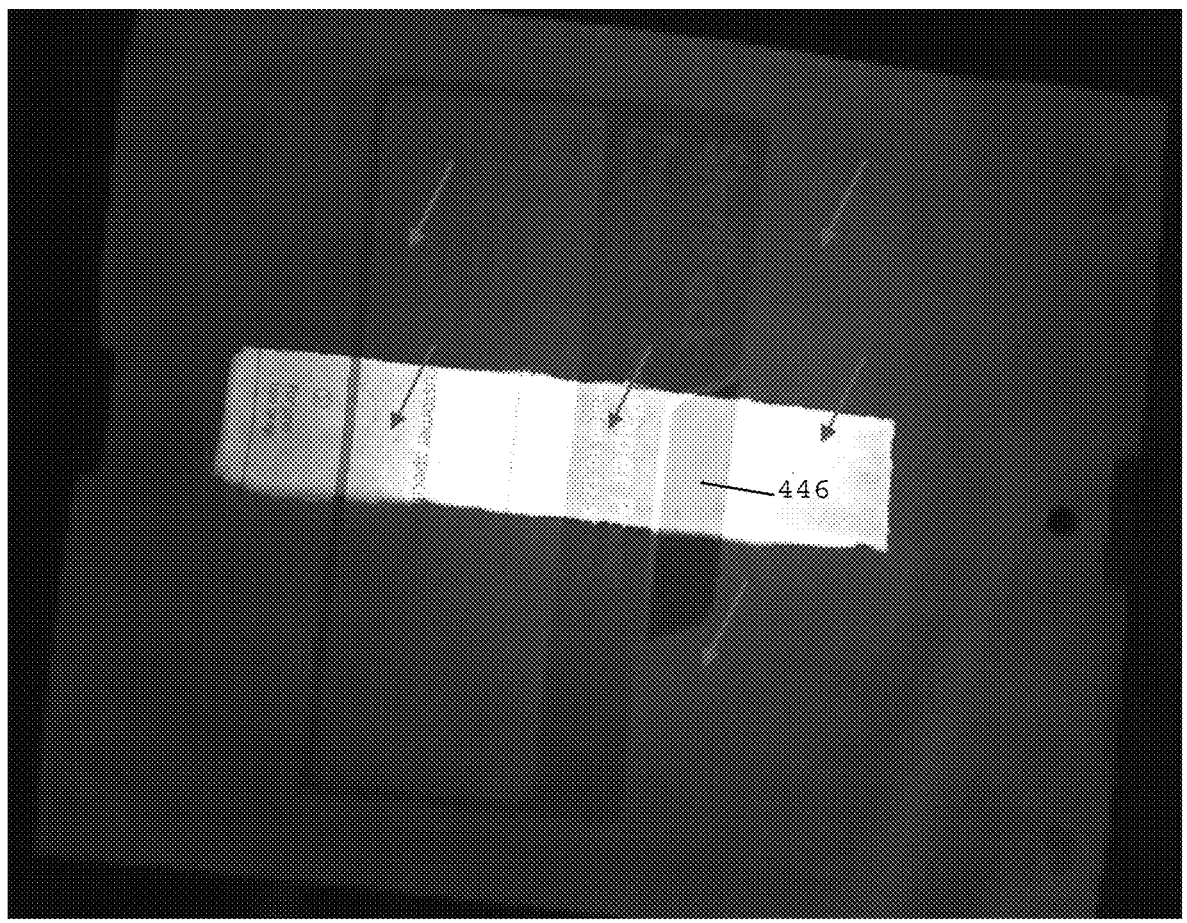
FIG. 12B shows the substrate of FIG. 12A exposed to UV light.
Figure 12C:
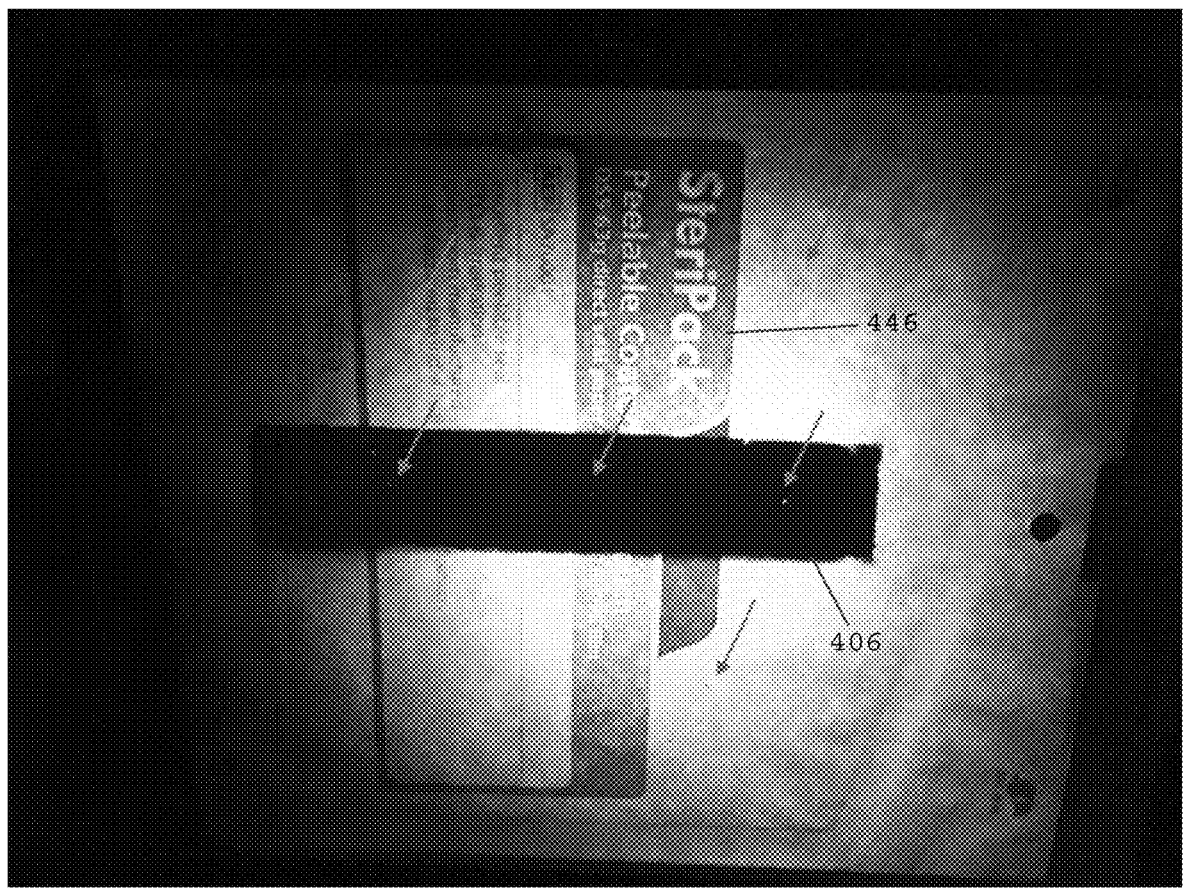
FIG. 12C shows a method of viewing the substrate of FIG. 12B through a camera having an optical filter for display on a monitor, in accordance with one embodiment of the present patent application.
Figures 1, 12C:
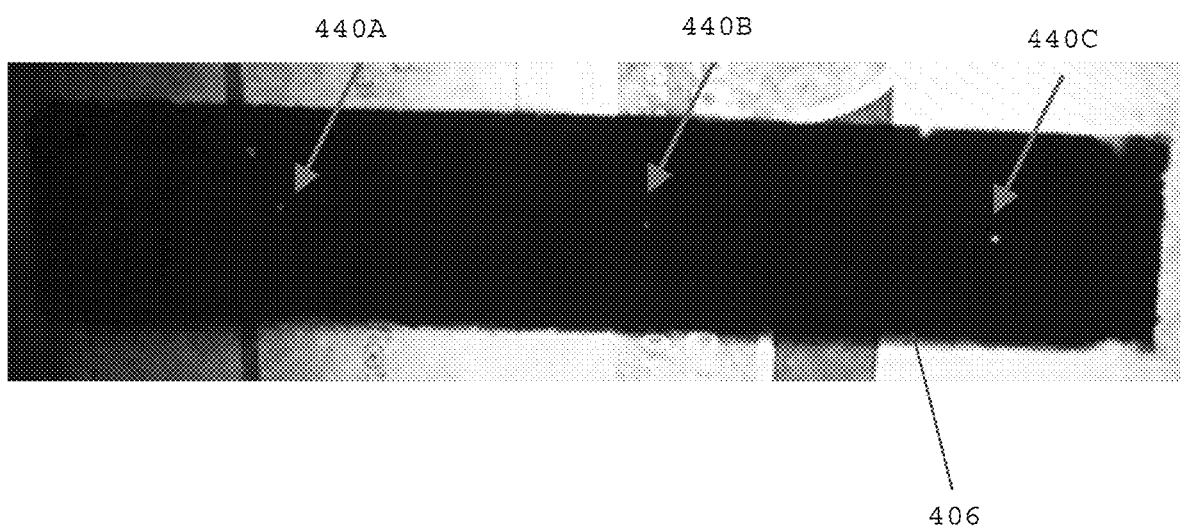

Referring to FIG. 12B, in one embodiment, UV light is directed at the second major surface (not shown) of the substrate 400 (i.e., from the underside of the substrate). In FIG. 12B, the optical filter is not utilized so that the indicia 446 printed on the first major surface of the substrate remains visible to the UV camera. In FIG. 12C, the optical filter is utilized so that the UV absorbent layer 406 appears as a black strip when an image of the substrate 400 is captured by the UV camera. The black strip 406 of UV absorbent material occludes the indicia 446 that underlies the UV absorbent material. The UV camera captures an image of pinhole defects 440A-440C that are located within the black strip 406 (FIG. 12C-1). The pinhole defects that are located outside the black strip are not as visible as the pinhole defects within the black strip. In one embodiment, the UV absorbent layer is applied over the entire surface of the substrate so that all of the defects may be readily observed on the monitor. The combination of the UV absorbent layer, the UV camera, and the optical filter enable any defects in the substrate to be identified during inspection.

Figure 13A:
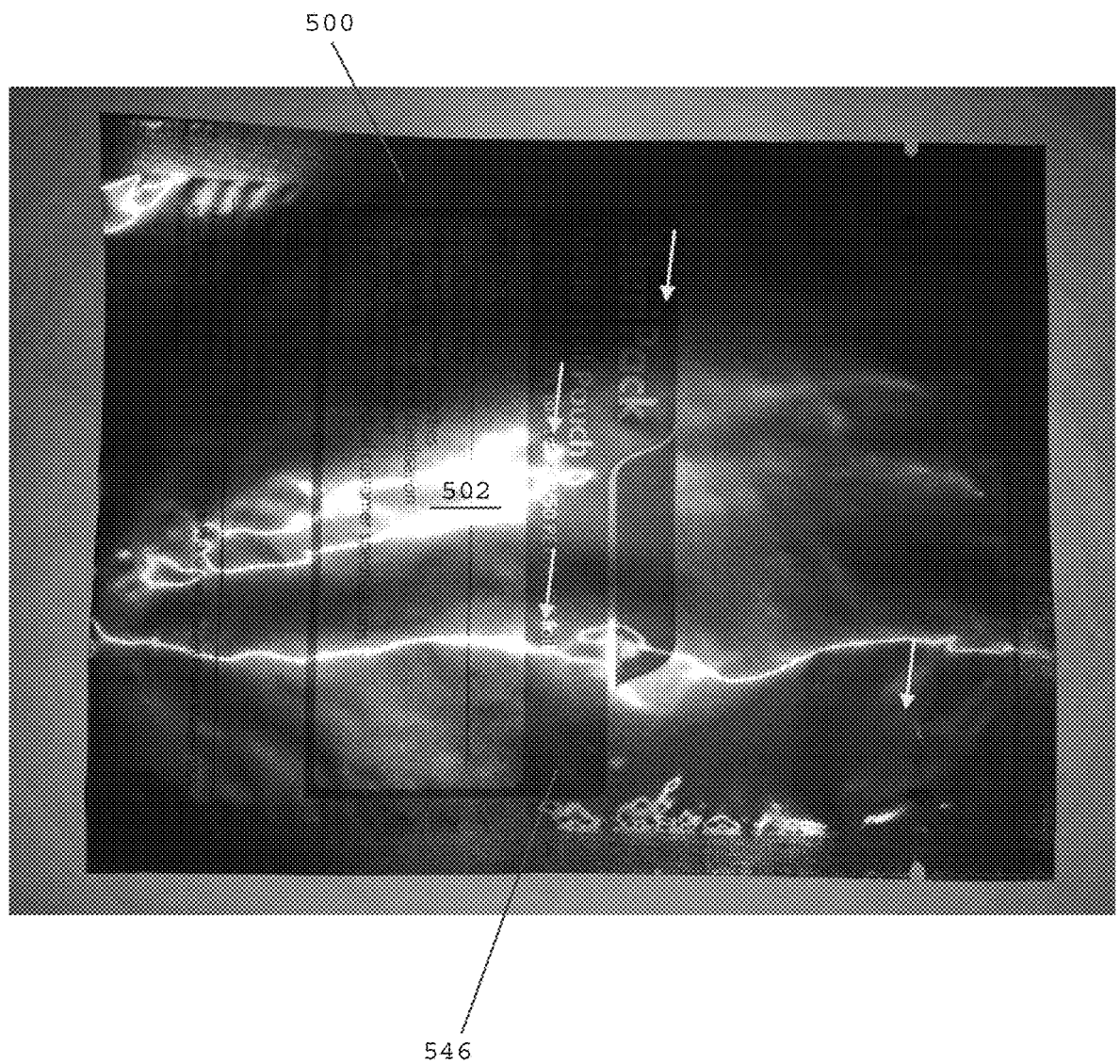
FIG. 13A shows a foil substrate that is covered with a UV absorbent layer, in accordance with one embodiment of the present patent application.

Referring to FIG. 13A, in one embodiment, a foil substrate 500 used for making a sterile, medical device package preferably has a first major surface 502 with indicia 546 printed thereon. A transparent, UV absorbent layer is applied over the first major surface 502 of the foil substrate 500. The foil substrate 500 has a number of pinhole defects formed therein that are highlighted by the arrows shown in FIG. 13A.

Figure 13B:
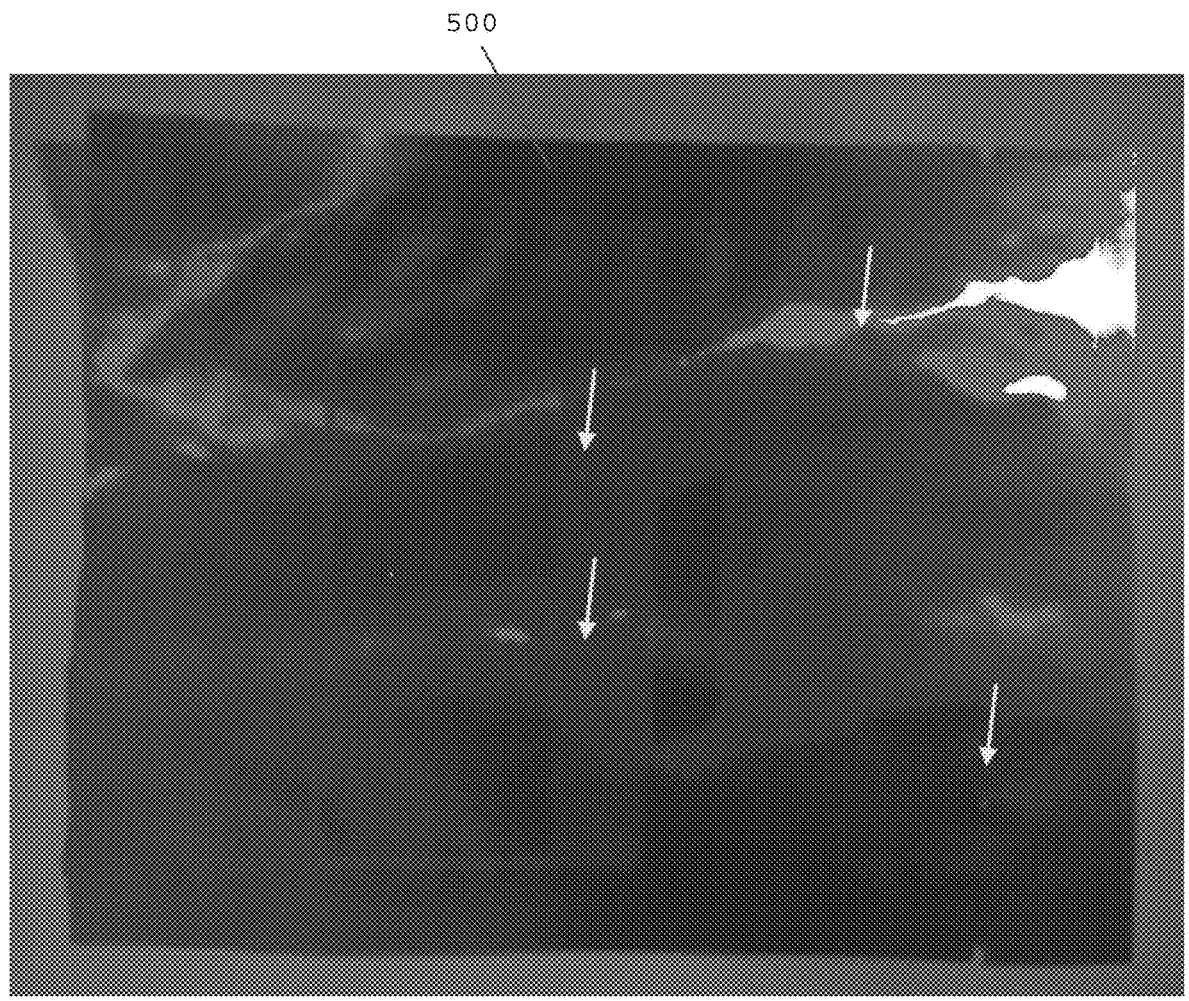
FIG. 13B shows the foil substrate of FIG. 13A exposed to UV light.
Figure 13C:
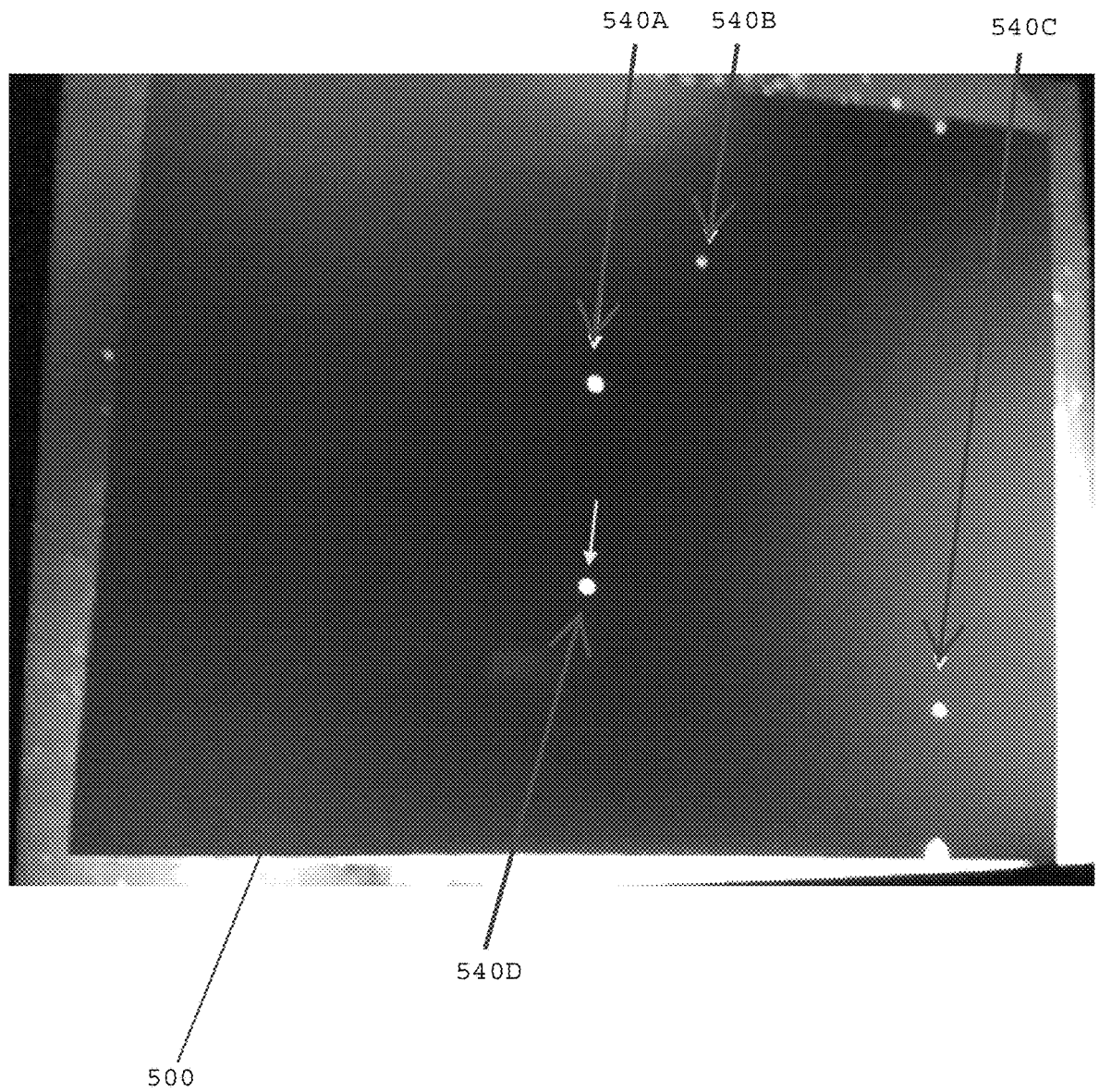
FIG. 13C shows a method of viewing the foil substrate of FIG. 13B through a camera having an optical filter for display on a monitor, in accordance with one embodiment of the present patent application.

Referring to FIG. 13B, in one embodiment, UV light is directed at the second major surface of the foil substrate 500 (i.e., from the underside of the foil substrate). In FIG. 13B, the optical filter is not utilized so that it remains difficult to identify and/or locate any pinhole defects that are present in the foil substrate. In FIG. 13C, the optical filter is utilized with a UV camera so that the UV absorbent layer that absorbs UV light appears as a black image on a monitor, which provides a stark contrast between the black surface and the white specks of light (i.e., the pinhole defects 540A-540D) that are present in the foil substrate 500. The combination of the UV absorbent layer, the UV camera, and the optical filter enable any defects in the flexible, foil substrate to be readily identified during inspection.

Figure 14:
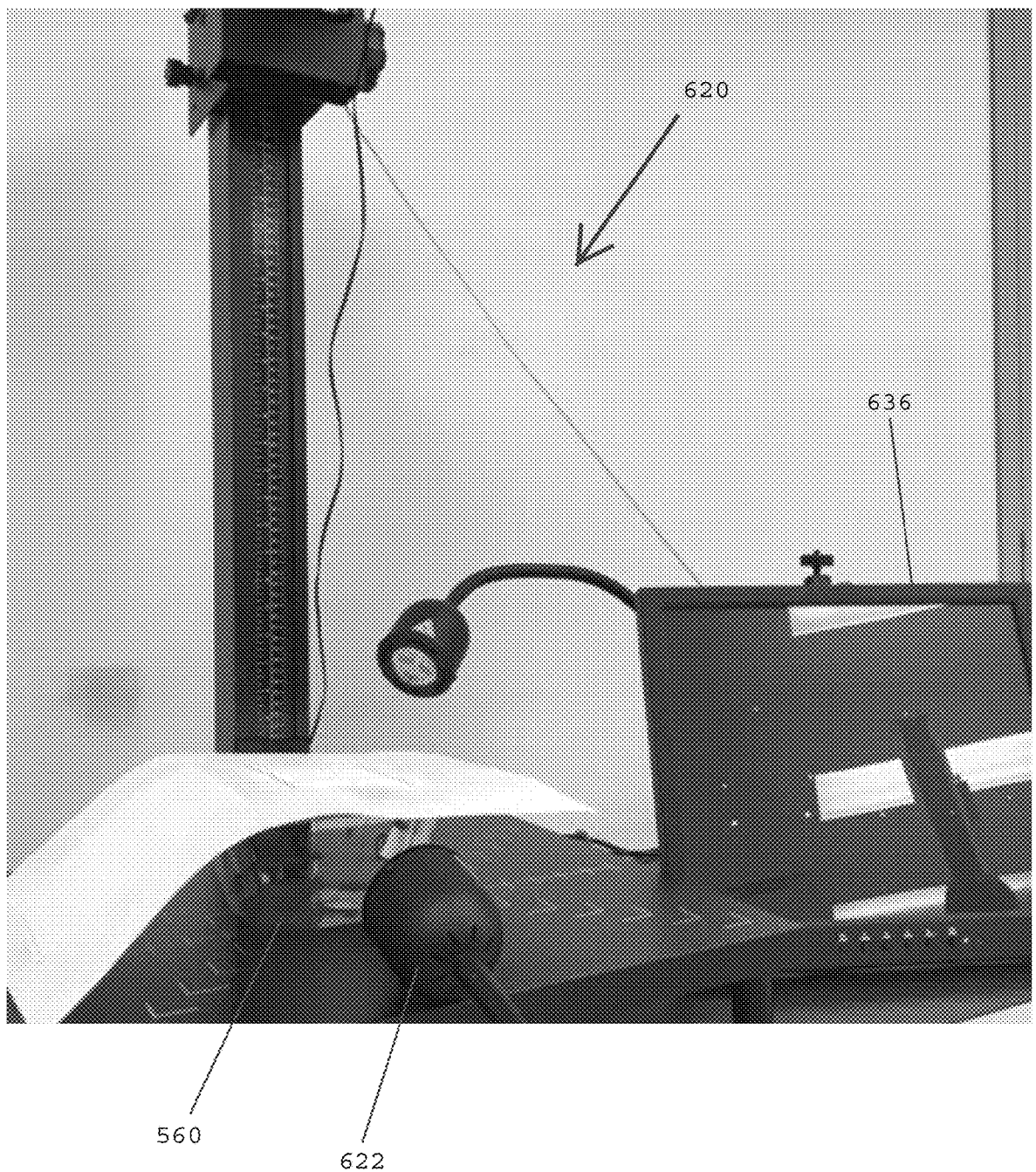
FIG. 14 shows a perspective view of a system for detecting defects in a medical device package having a substrate and a thermoformed container, in accordance with one embodiment of the present patent application.
Figure 15:
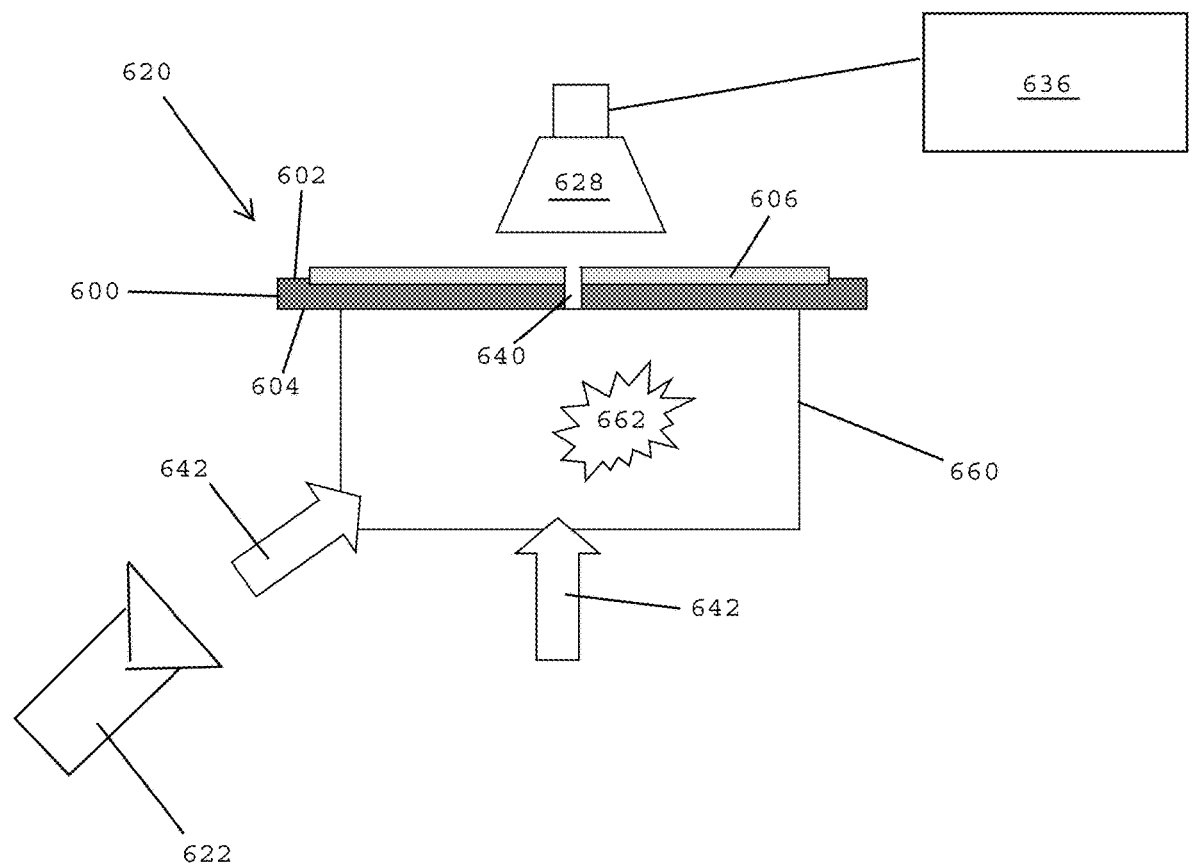
FIG. 15 shows a schematic view of the system shown in FIG. 14.

Referring to FIGS. 14 and 15, in one embodiment, a system 620 for detecting defects in a substrate may be utilized with medical device packages having a container 660, such as a thermoformed container, that holds a medical device 662.

In one embodiment, the container 660 may have a container opening at an upper end thereof that is sealed by a substrate 600. In one embodiment, the substrate 600 has a first major surface 602 and a second major surface 604. The substrate 600 may have microscopic pores that enable sterilization but prevent bacteria from passing through the substrate (e.g., a TYVEK® substrate). The first major surface 602 is preferably covered by a UV absorbent layer 606 that is adapted to absorb UV light. In one embodiment, the second major surface 604 of the substrate 600 is sealed over the opening of the thermoformed container 660 for sealing the medical device 662 inside the thermoformed container.

In one embodiment, the substrate 600 is screened for defects (e.g., openings larger than 10 microns) by utilizing a UV light source 622 to generate UV light 642 that passes through the walls of the container 660 and strikes the second major surface 604 of the substrate 600. The UV light 642 is absorbed by the UV absorbable coating 606 covering the first major surface 602 of the substrate 600. In one embodiment, the substrate 600 has a pinhole defect 640 that enables the UV light to pass through the substrate 600 for being detected by the UV camera 628. The UV camera 628 transmits captured images of the substrate 600 to a monitor 636 to show any defects present in the substrate 600.

In one embodiment, the container 660 may be a clear or transparent container through which visible light may pass for observing the medical device 662 located inside the thermoformed container 660. In one embodiment, the container 660 may be opaque so that it does not provide visibility of the medical device contained therein. In any event, the UV light may pass through the walls of the container for checking for defects in the walls of the container and/or the substrate that seals the container opening.

Figure 16A:
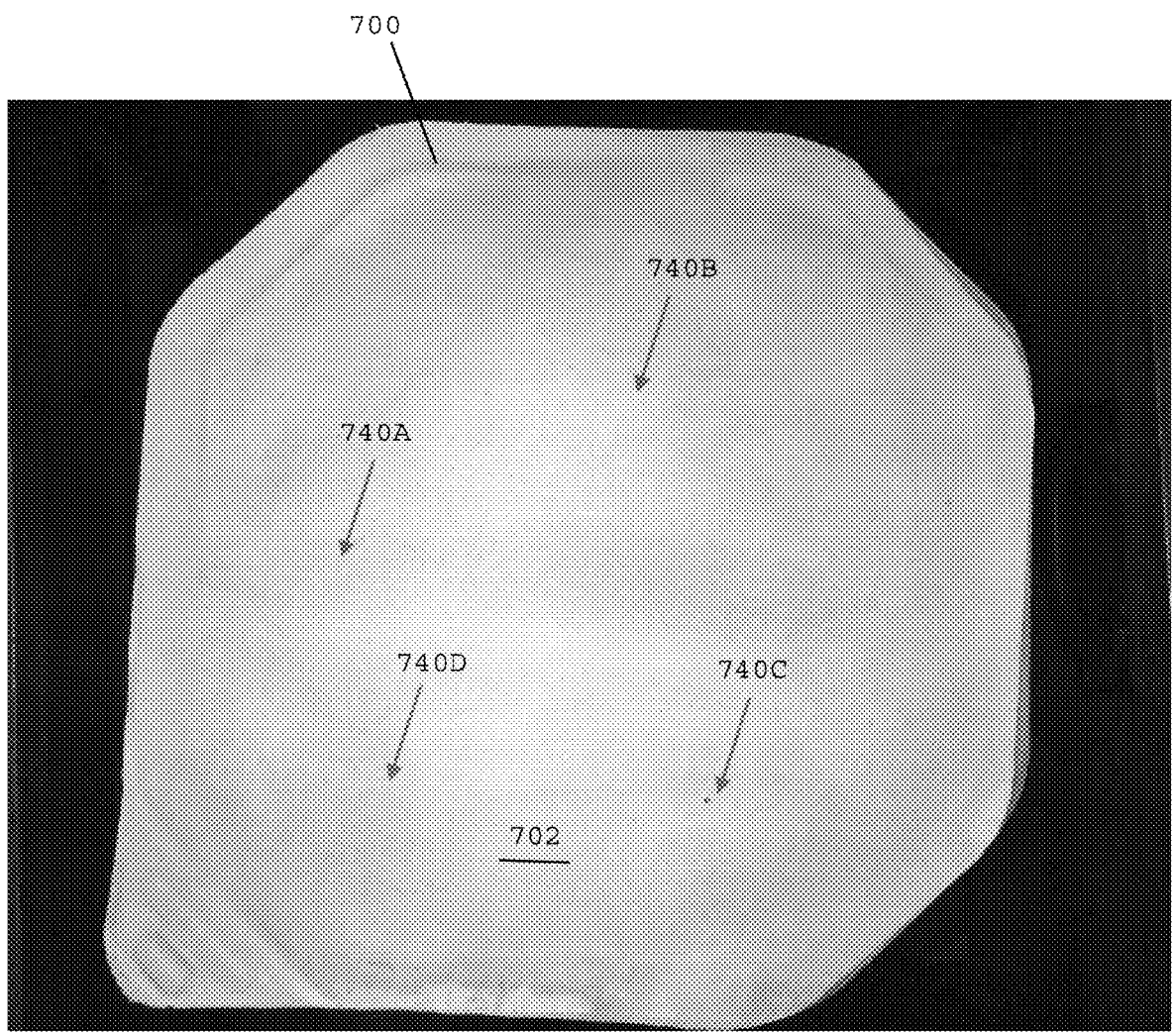
FIG. 16A shows a top plan view of a substrate used in medical device packages, in accordance with one embodiment of the present patent application.

Referring to FIG. 16A, in one embodiment, a substrate 700 preferably has a first major surface that is covered by a UV absorbent layer. The UV absorbent layer may be transparent to visible light. The substrate has pinhole defects 740 that are highlighted by the arrows shown in FIG. 16A. The pinhole defects may not be visible to the human eye. In one embodiment, the substrate 700 is used for sealing the top of a thermoformed container (e.g., the thermoformed container 660 shown in FIG. 15).

Figure 16B:
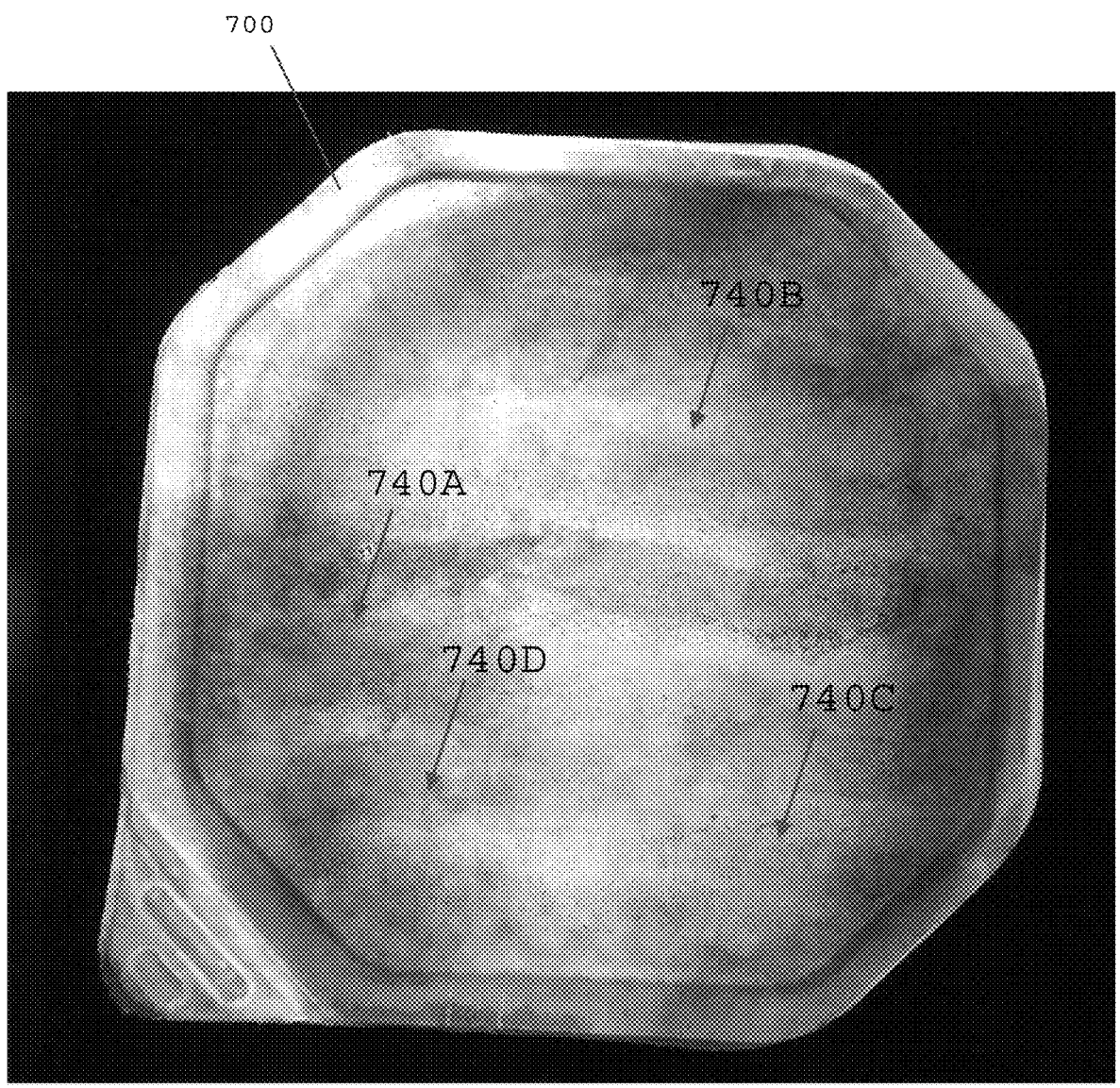
FIG. 16B shows the substrate of FIG. 16A exposed to UV light.
Figure 16C:
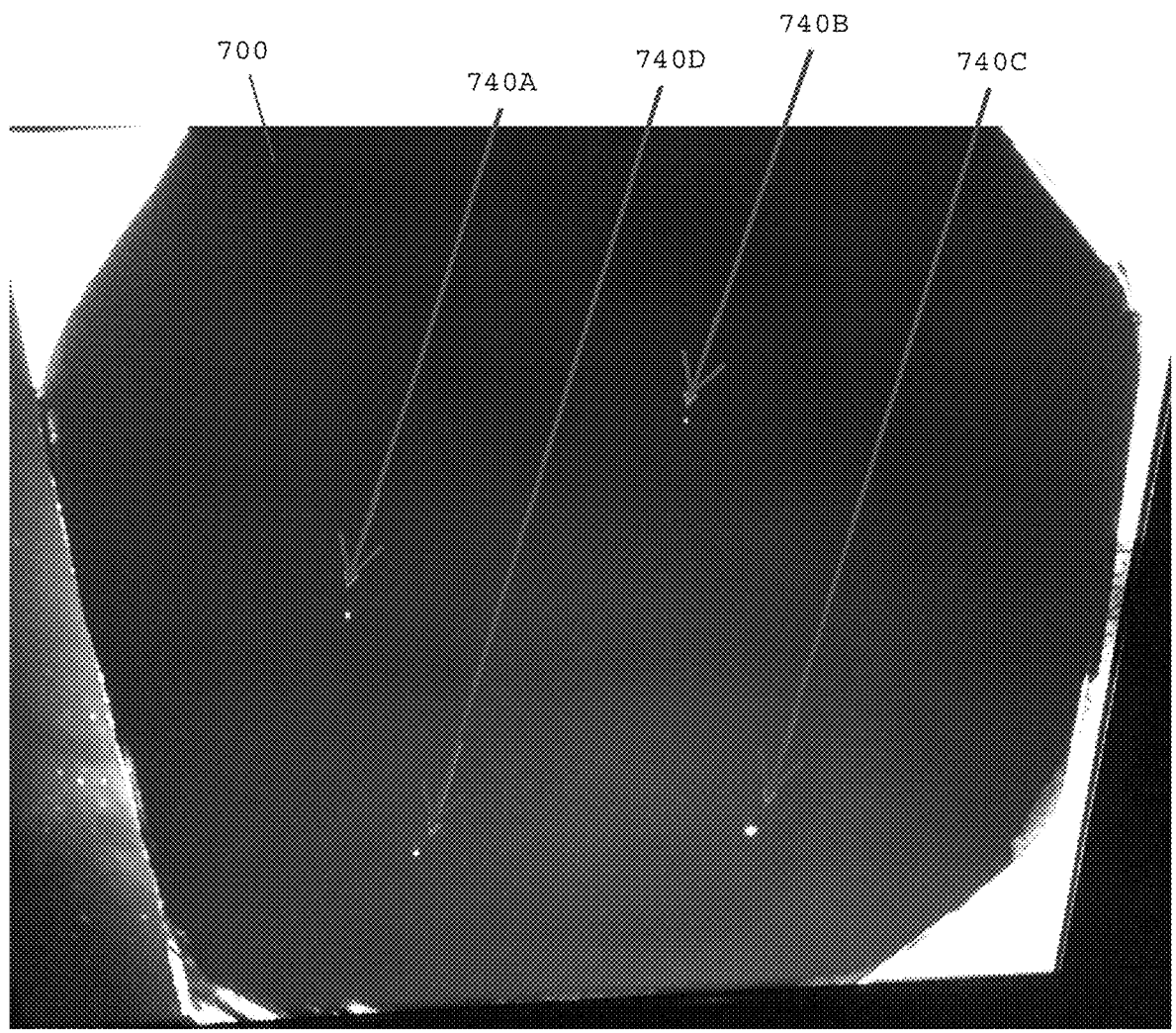
FIG. 16C shows a method of viewing the substrate of FIG. 16B through a camera having an optical filter for display on a monitor, in accordance with one embodiment of the present patent application.

Referring to FIG. 16B, UV light is directed at the substrate 700. In FIG. 16B, the optical filter is not utilized so that it remains difficult to identify and/or locate any pinhole defects that are present in the substrate. In FIG. 16C, the optical filter is utilized with a UV camera so that the UV absorbent layer appears as a black image on a monitor, which provides a stark contrast between the black surface and the pinhole defects 740A-740D that are present in the substrate 700, which appear on a monitor as specks of light. The combination of the UV absorbent layer, the UV camera, and the optical filter enable any defects in the flexible, substrate to be readily identified during inspection.

Figure 17A:
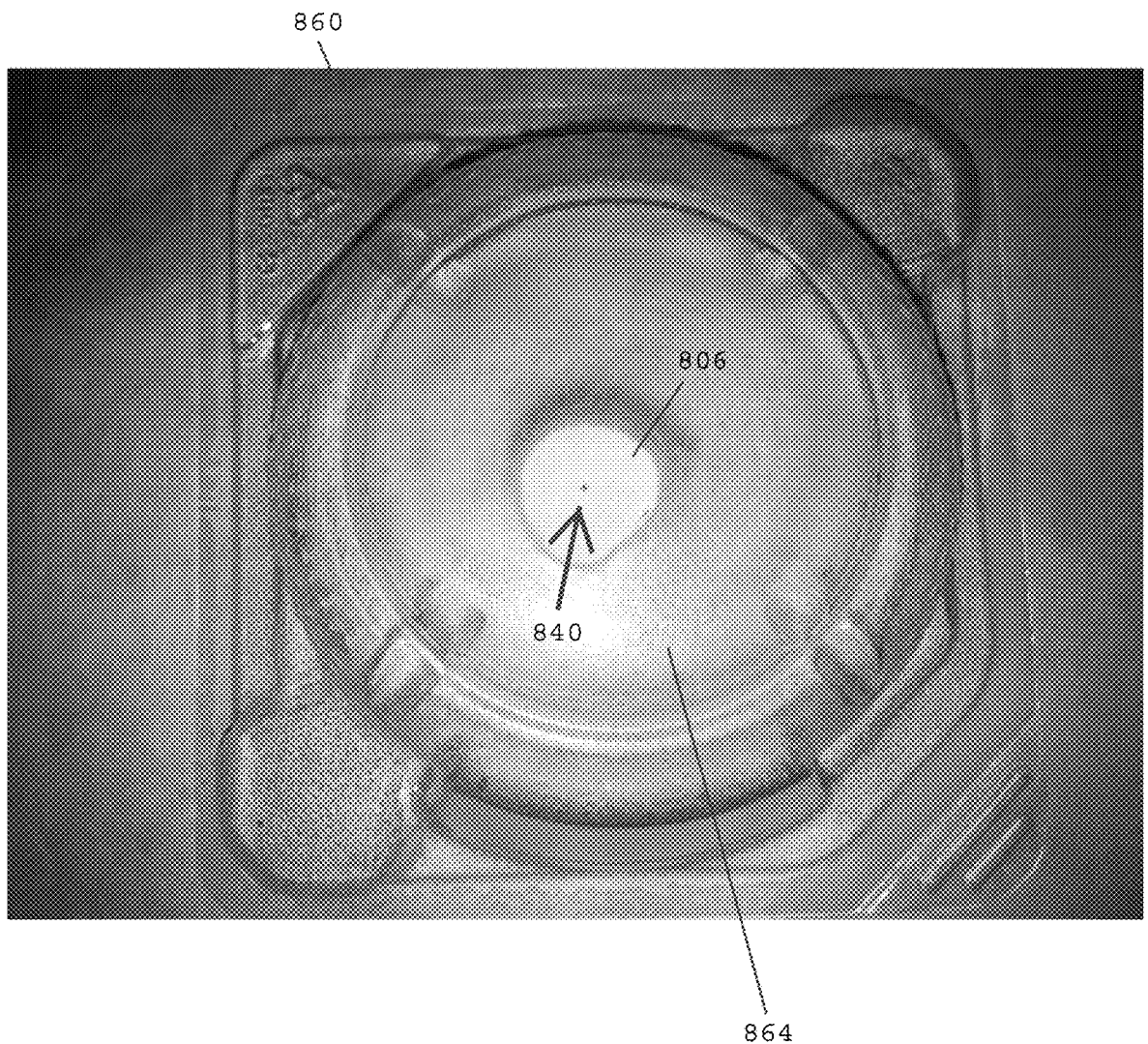
FIG. 17A shows a bottom view of a thermoformed container having a bottom wall with a UV absorbent layer, in accordance with one embodiment of the present patent application.

In one embodiment, the system disclosed herein may be used for locating and/or identifying defects in the walls of a thermoformed container 860. Referring to FIG. 17A, in one embodiment, the thermoformed container 860 preferably has a bottom wall 865 that is at least partly covered with a UV absorbent layer 806. The bottom wall 865 has a pinhole defect 840 formed therein.

Figure 17B:
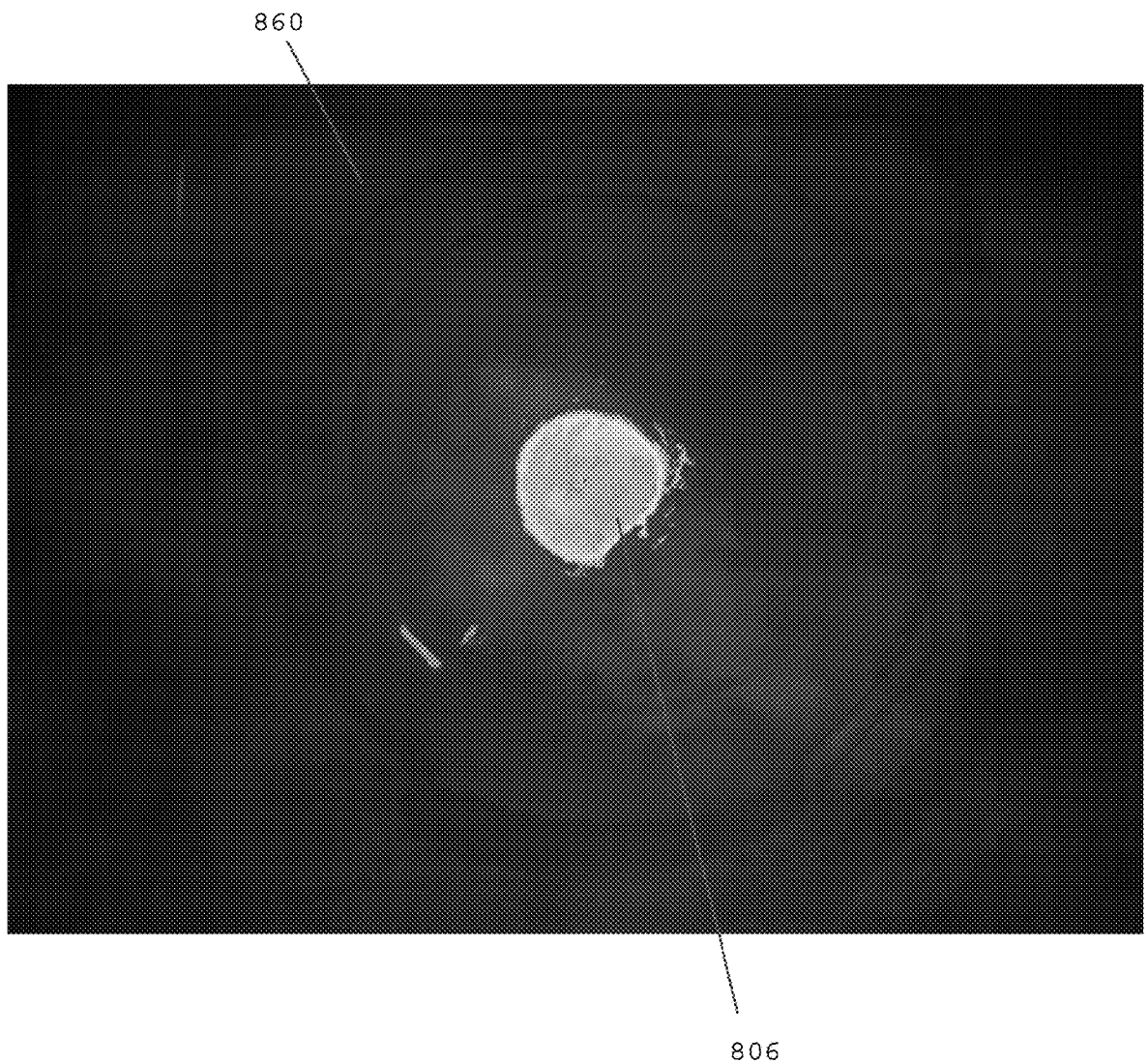
FIG. 17B shows the thermoformed container of FIG. 17A exposed to UV light.
Figure 17C:
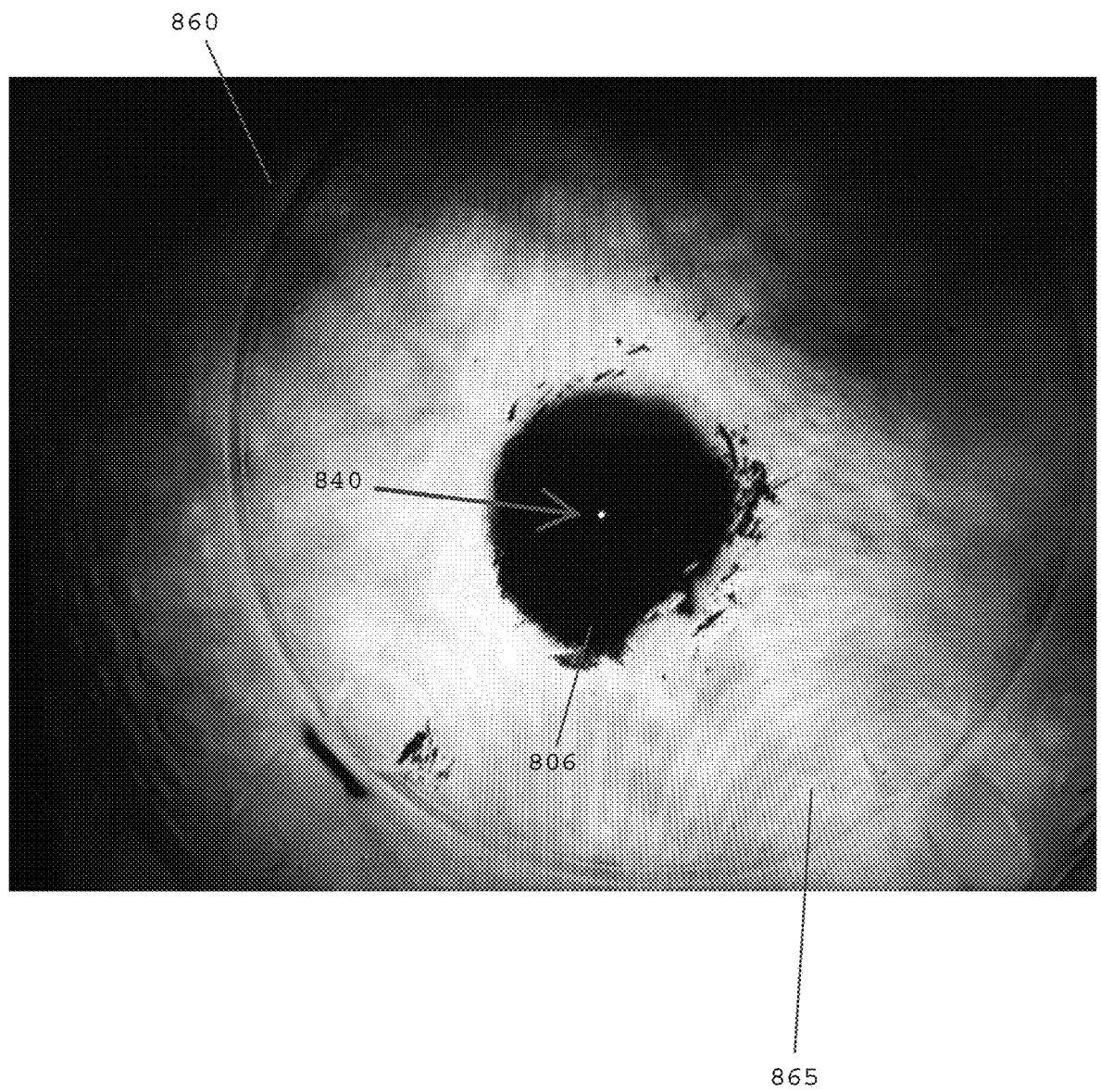
FIG. 17C shows a method of viewing the thermoformed container of FIG. 17B through a camera having an optical filter for display on a monitor, in accordance with one embodiment of the present patent application.

Referring to FIG. 17B, UV light is directed at the thermoformed container 860. In FIG. 17B, the optical filter is not utilized so that it remains difficult to identify and/or locate any pinhole defects that are present in the substrate. In FIG. 17C, the optical filter is utilized with a UV camera so that the UV absorbent layer appears as a black image on a monitor, which provides a stark contrast between the black surface generated by the UV coating and the pinhole defect 840 that is present in the bottom wall 865 of the thermoformed container 860, which appears on a monitor as a speck of light within a black background. The combination of the UV absorbent layer, the UV camera, and the optical filter enable any defects in the flexible, substrate to be readily identified during inspection.

Figure 18A:
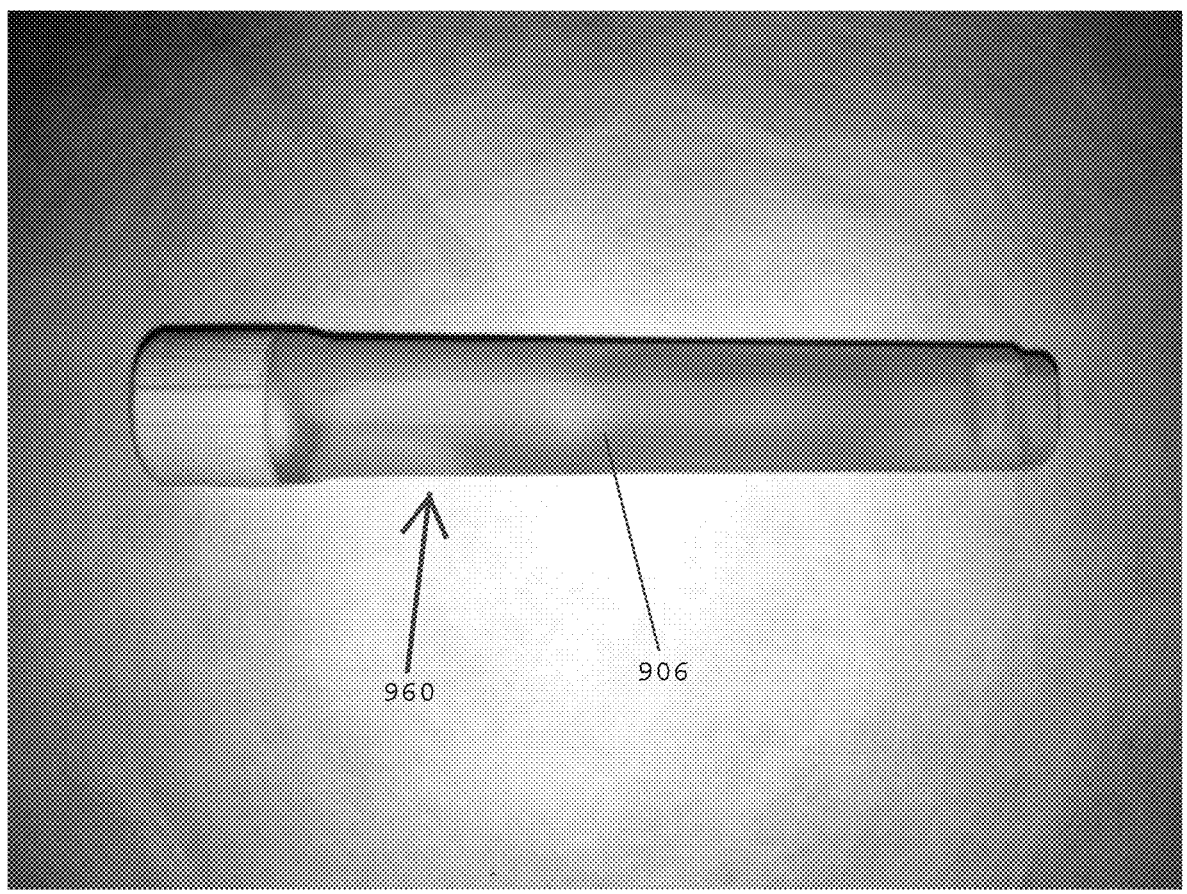
FIG. 18A shows a medical device tube having an outer surface that is covered by a UV absorbent layer, in accordance with one embodiment of the present patent application.

In one embodiment, the system disclosed herein may be used for locating and/or identifying defects in the walls of a three dimensional container such as a tube. Referring to FIG. 18A, in one embodiment, the tube 960 has an outer surface that is covered with a UV absorbent layer 906.

Figure 18B:
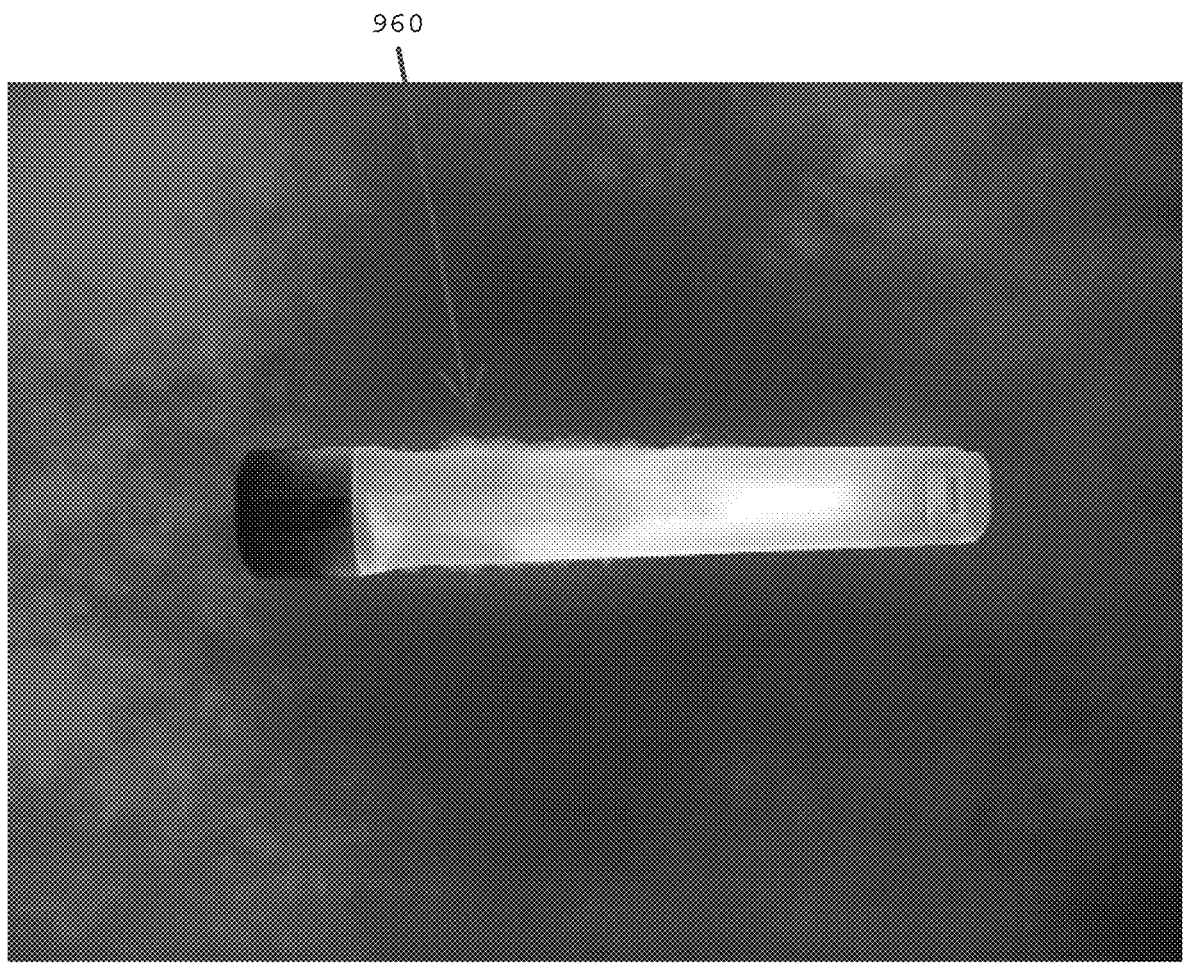
FIG. 18B shows the medical device tube of FIG. 18A exposed to UV light.
Figure 18C:
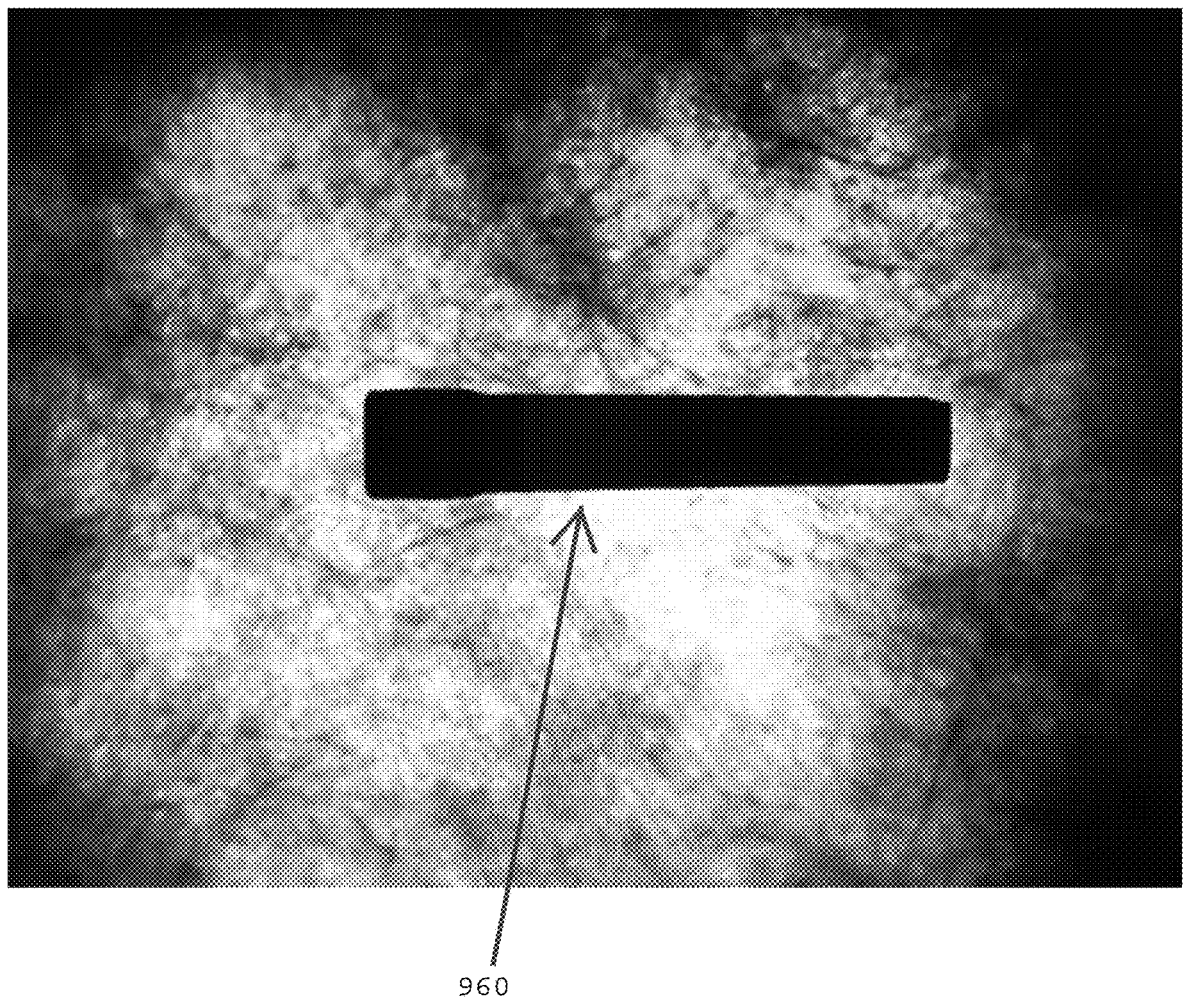
FIG. 18C shows a method of viewing the medical device tube of FIG. 18B through a camera having an optical filter for display on a monitor, in accordance with one embodiment of the present patent application.

Referring to FIG. 18B, UV light is directed at the tube 960. In FIG. 18B, the optical filter is not utilized so that it remains difficult to identify and/or locate any pinhole defects that are present in the tube. In FIG. 18C, the optical filter is utilized with a UV camera so that the UV absorbent layer appears as a black image on a monitor, which provides a stark contrast between the black surface generated by the UV coating and any defects that may be present in the walls of the tube 960. Referring to FIG. 18C, the image of the tube 960 captured by the UV camera is completely black with no white spots or specks of light, which indicates that there are no defects in the tube 960. In one embodiment, the combination of the UV absorbent layer, the UV camera, and the optical filter enable any defects in the tube 960 to be readily identified during inspection.

Figure 19A:
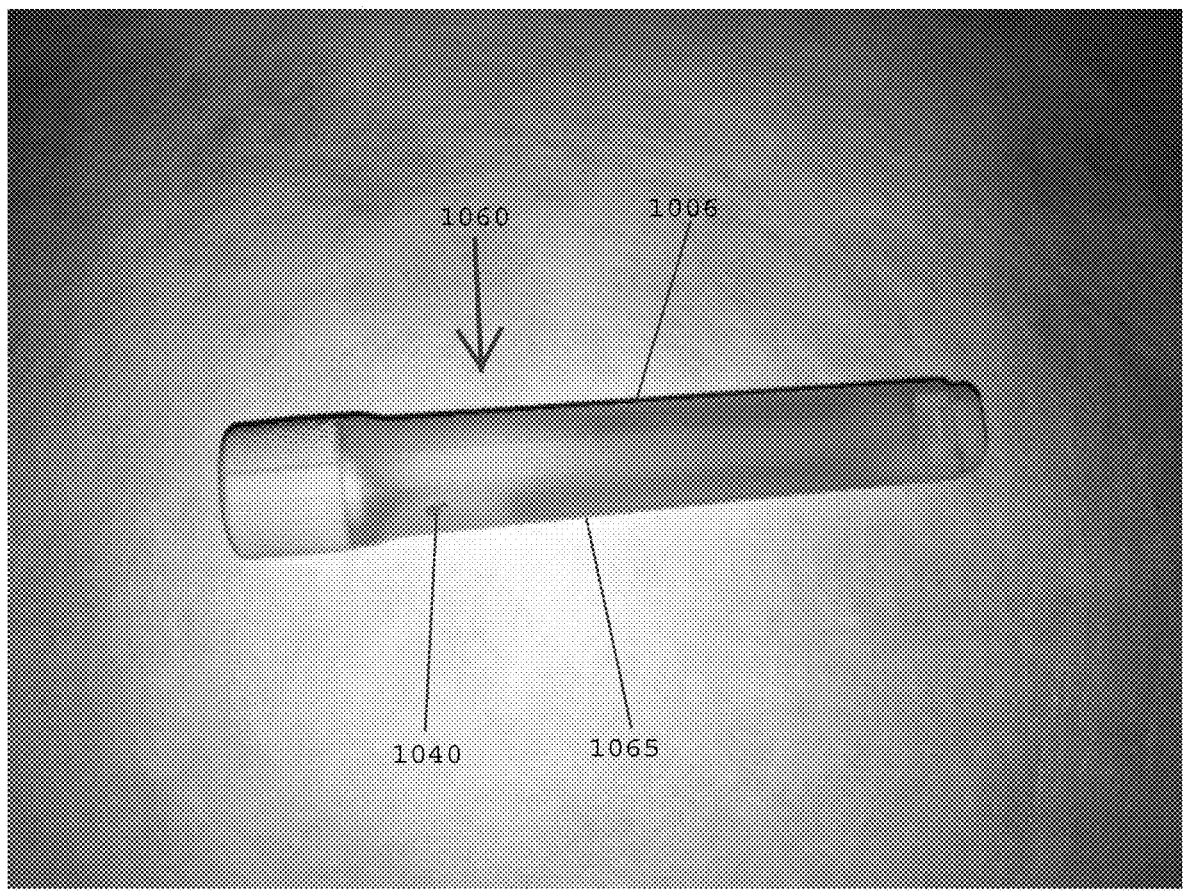
FIG. 19A shows a medical device tube having an outer surface that is covered by a UV absorbent layer, in accordance with one embodiment of the present patent application.

Referring to FIG. 19A, in one embodiment, a tube 1060 preferably has an outer wall 1065 that is covered with a UV absorbent layer 1006. The outer wall 1065 has a hole 1040 formed therein, which constitutes a defect in the tube 1060.

Figure 19B:
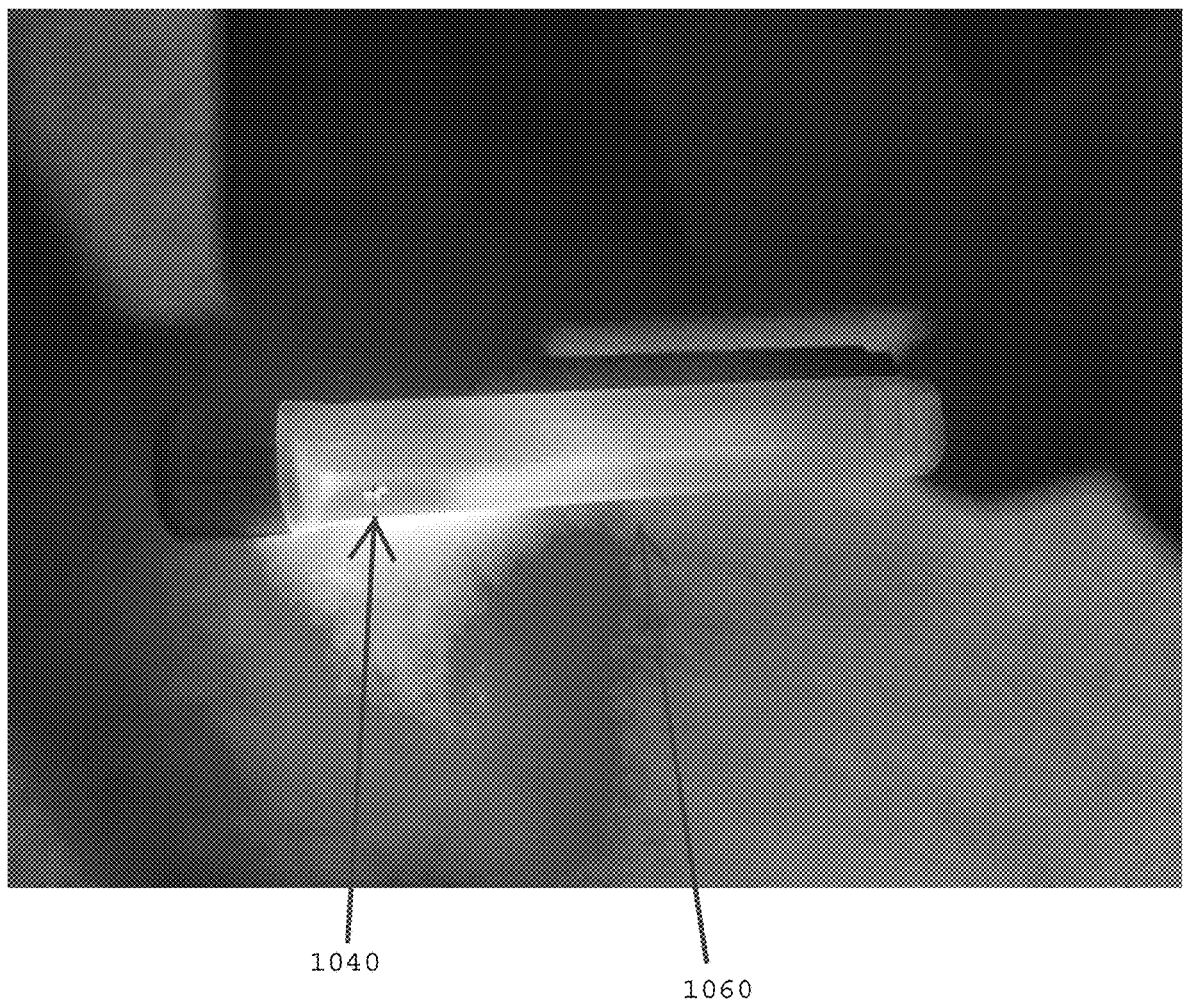
FIG. 19B shows the medical device tube of FIG. 19A exposed to UV light.
Figure 19C:
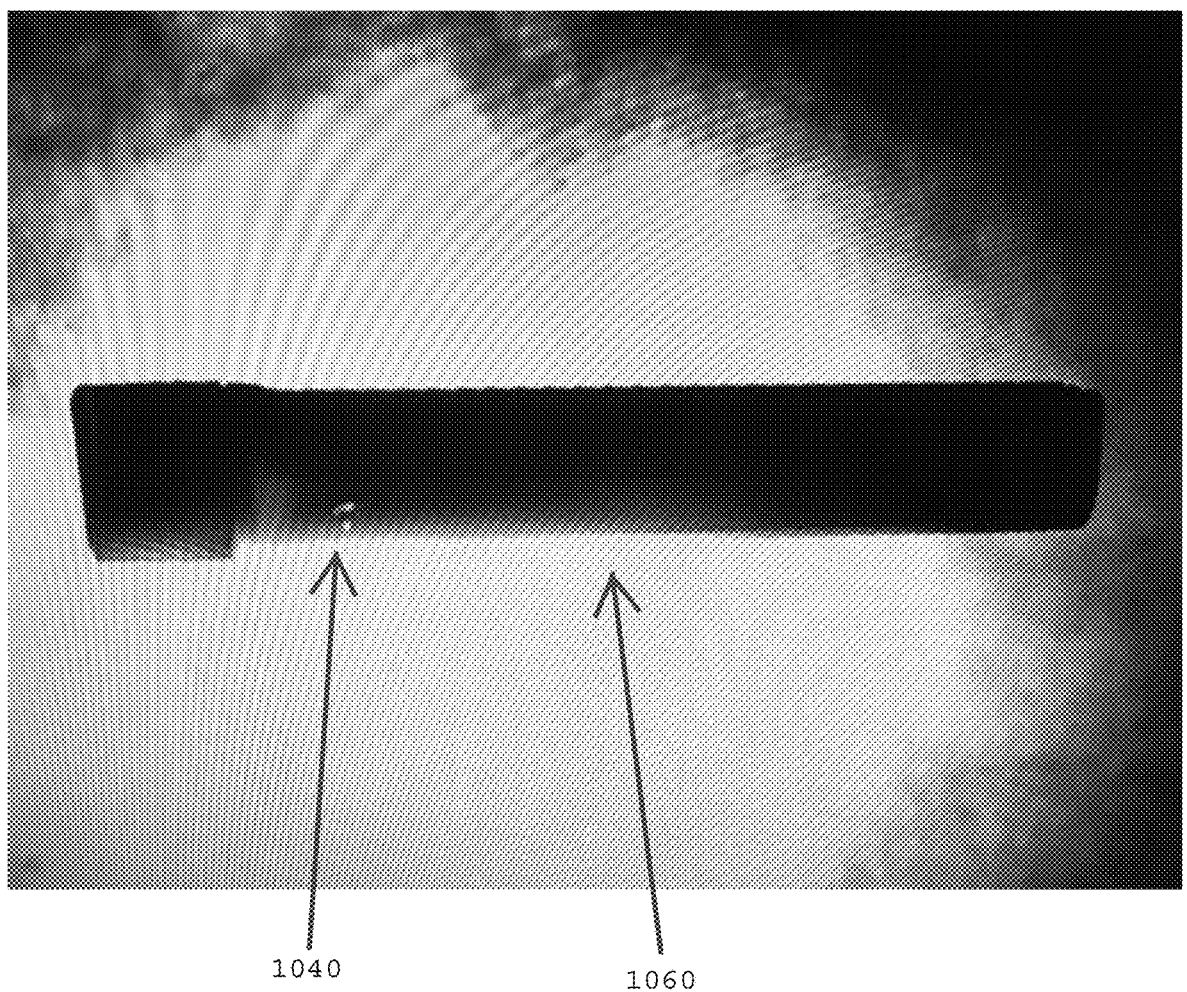
FIG. 19C shows a method of viewing the medical device tube of FIG. 19B through a camera having an optical filter for display on a monitor, in accordance with one embodiment of the present patent application.

Referring to FIG. 19B, UV light is directed at the tube 1060. In FIG. 19B, the optical filter is not utilized so that it remains difficult to identify and/or locate the hole defect 1040 that is present in the tube 1060. In FIG. 19C, the optical filter is utilized with a UV camera so that the UV absorbent layer appears as a black image on a monitor, which provides a stark contrast between the black surface generated by the UV coating and the white pinhole defect 1040 that is present in the outer wall 1065 of the tube 1060. The combination of the UV absorbent layer, the UV camera, and the optical filter enable any defects in the tube 1060 to be readily identified during inspection.

In one embodiment, the present patent application is directed to detecting defects in substrates used for medical device packages. In one embodiment, the present patent application discloses that an opening that is larger than 10 microns will be considered to be a defect. In other embodiments, however, a substrate having an opening with a size that is less than 10 microns may be considered to be a defect. For example, a substrate having an opening with a size of five (5) microns may be considered to be defective. In still other embodiments, a substrate having a detected opening having a size that is slightly larger than 10 microns (e.g., 12 microns) may be deemed acceptable.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A method of evaluating the integrity of a substrate used for medical device packaging comprising:
    applying a UV absorbent layer over a surface of a substrate;
    placing said substrate over a UV reflective surface that is adapted to reflect UV light;
    directing UV light toward said UV absorbent layer applied over said surface of said substrate and said UV reflective surface, wherein said UV absorbent layer applied over said surface of said substrate absorbs the directed UV light that strikes said UV absorbent layer;
    detecting with a camera any of the directed UV light that passes through a pinhole defect in said UV absorbent layer applied over said surface of said substrate and that is then reflected by said UV reflective surface back through said pinhole defect to said camera.

2. The method as claimed in claim 1, wherein said substrate is porous.

3. The method as claimed in claim 1, wherein said substrate is flexible and is made of a material selected from the group consisting of synthetic fibers, polyethylene fibers, flashspun high-density polyethylene fibers, polymers, paper, and foil.

4. The method as claimed in claim 1, wherein said UV absorbent layer absorbs light in a spectrum that matches the wavelength of said UV light directed toward said substrate.

5. The method as claimed in claim 4, wherein said UV absorbent layer is transparent in light in the visible spectrum.

6. The method as claimed in claim 1, wherein said substrate has a first major surface and a second major surface, and wherein the applying a UV absorbent layer comprises coating at least one of the first and second major surfaces of said substrate with a UV absorbent material.

7. The method as claimed in claim 1, further comprising providing an optical filter in the optical path of said camera, wherein said optical filter transmits the reflected UV light to said camera and blocks visible and infrared light from reaching said camera.

8. The method as claimed in claim 7, further comprising displaying images of the reflected UV light on a visual display screen.

9. The method as claimed in claim 1, further comprising:
    rejecting said substrate if the reflected UV light detected by said camera indicates that said substrate has at least one opening having a size that is greater than or equal to 10 microns; and
    accepting said substrate if the reflected UV light detected by said camera indicates that said substrate has no openings that are greater than or equal to 10 microns.

10. A method of evaluating the integrity of a substrate used in medical device packaging comprising:
    providing a flexible, porous substrate having a first major surface, and a second major surface;
    applying a UV absorbent layer over at least one of the first and second major surfaces of said flexible, porous substrate;

placing said flexible, porous substrate over a UV reflective surface that is adapted to reflect UV light;

directing UV light toward said UV absorbent layer applied over said flexible, porous substrate and said UV reflective surface, wherein said UV absorbent layer absorbs said directed UV light that strikes said UV absorbent layer;

detecting with a UV sensitive camera any of said directed UV light that passes through a pinhole defect in said UV absorbent layer and that is then reflected by said UV reflective surface back through said pinhole defect to said camera.

11. The method as claimed in claim 10, further comprising displaying images of the reflected UV light that is detected by said UV sensitive camera on a visual display screen.

12. The method as claimed in claim 10, further comprising:

rejecting said flexible, porous substrate if the reflected UV light that is detected by said UV sensitive camera indicates that said flexible, porous substrate has at least one opening having a size that is greater than or equal to 10 microns; and accepting said flexible, porous substrate if the reflected UV light detected by said camera indicates that said flexible, porous substrate has no openings that are greater than or equal to 10 microns.

13. The method as claimed in claim 10; further comprising providing an optical filter in the optical path of said UV sensitive camera, wherein said optical filter transmits the reflected UV light to said UV sensitive camera and blocks visible and infrared light from reaching said UV sensitive camera.

14. A method of evaluating the integrity of a substrate used in medical device packaging comprising:

applying a UV absorbent layer over a major surface of a substrate;

directing UV light toward said substrate, wherein said UV absorbent layer absorbs the UV light that strikes said UV absorbent layer;

detecting with a UV sensitive camera any of said directed UV light that passes through a pinhole defect in said UV absorbent layer and that is then reflected by said UV reflective surface back through said pinhole defect to said UV sensitive camera;

rejecting said substrate if the reflected UV light detected by said UV sensitive camera indicates that said pinhole defect has a size that is greater than or equal to 10 microns.

15. The method as claimed in claim 14, wherein said substrate is made of materials selected from the group consisting of synthetic fibers, polyethylene fibers, flashspun high-density polyethylene fibers, paper, foil, polymers; and thermoformed polymers.

16. The method as claimed in claim 15, wherein said UV sensitive camera is configured to detect light within the ultraviolet light spectrum and block light within visible and infrared light spectrums.

17. The method as claimed in claim 14, wherein said substrate comprises a thermoformed container having a container opening adapted to receive a medical device, and wherein said method further comprises sealing a flexible substrate over the container opening of said thermoformed container.

18. A system for evaluating the integrity of a substrate used in medical device packaging comprising:

at least one UV light source that generates UV light having a wavelength that lies within the UV light spectrum;

a UV absorbent material that covers a first major surface of said substrate, wherein said UV absorbent material absorbs light that matches the wavelength of the UV light generated by said UV light source;

a UV reflective surface that is adapted to reflect the UV light generated by said UV light source;

a UV sensitive camera that is configured to detect any of the reflected UV light that is not absorbed by said UV absorbent material and that passes through said pinhole defect in said UV absorbent material, wherein said UV sensitive camera is configured to block light within visible and infrared light spectrums;

a visual display for displaying images of the reflected UV light that is not absorbed by said UV absorbent material, that passes through a pinhole defect in said UV absorbent material, and that is detected by said UV sensitive camera.

19. The system as claimed in claim 18, further comprising an optical filter in the optical path of said UV sensitive camera, wherein said optical filter transmits the reflected UV light to said UV sensitive camera and blocks visible and infrared light from reaching said UV sensitive camera.

20. The system as claimed in claim 18, further comprising:

said substrate being disposed between said UV sensitive camera and said UV reflective surface.

* * * * *